(12) United States Patent
Wilusz et al.

(10) Patent No.: US 6,627,398 B1
(45) Date of Patent: Sep. 30, 2003

(54) SYSTEM FOR REPRODUCING AND MODULATING STABILITY AND TURNOVER OF RNA MOLECULES

(75) Inventors: Jeffrey Wilusz, South Amboy, NJ (US); Lance P. Ford, Cranford, NJ (US)

(73) Assignee: University of Medicine and Dentistry of New Jersey, New Brunswick, NJ (US)

(*) Notice: Subject to any disclaimer, the term of this patent is extended or adjusted under 35 U.S.C. 154(b) by 0 days.

(21) Appl. No.: 09/320,609

(22) Filed: May 26, 1999

Related U.S. Application Data

(60) Provisional application No. 60/086,675, filed on May 26, 1998.

(51) Int. Cl.[7] .......................... C12Q 1/68; G01N 33/50; C12N 5/22; C07H 21/02
(52) U.S. Cl. .......................... 435/6; 435/7.21; 435/367; 435/372; 435/455; 536/25.41
(58) Field of Search ............................... 536/23.1, 24.1, 536/24.5, 25.41; 435/6, 7.21, 367, 372, 455

(56) References Cited

U.S. PATENT DOCUMENTS

| | | | |
|---|---|---|---|
| 5,264,372 A | * 11/1993 | Beaumont | 436/504 |
| 5,733,728 A | 3/1998 | Port et al. | 435/6 |

FOREIGN PATENT DOCUMENTS

| | | |
|---|---|---|
| WO | WO93/23531 | 11/1993 |
| WO | WO95/29244 | 11/1995 |

OTHER PUBLICATIONS

Bernstein, P, et al, "The poly(A)–Poly(A)–binding protein complex is a major determinant of mRNA stability in Vitro", Molecular and Cellular Biology, Feb. 1989, Vol 9, No. 2, pp 659–670.*

Krikorian, C, et al, "In vitro mRNA degradation system to study the virion host shutoff function of herpes simplex virus", Journal of Virology, Jan. 1991, Vol 65, pp 112–122.*

Chen, C, et al, "mRNA decay mediated by two distinct AU–rich elements from c–fos and granulocyte–macrophage colony–stimulating factor transcripts: different deadenylation kinetics and uncoupling from translation", Mol Cell Biol, Oct. 1995, 15(10), p5777–88.*

Zhang, et al, "Purification, characterization, and cDNA cloning of an AU–rich element RNA–binding protein, AUF1", Mol Cell Biol, Dec. 1998, vol 13, no 12, pp 7652–65.*

Myer, et al, "Identification of HuR as a protein implicated in AUUUA–mediated mRNA decay", EMBO, Vol 16, no 8, Apr. 15, 1997, pp 2130–2139.*

Nakagawa, et al, "AUH, a gene encoding an AU–specific RNA binding protein with intrinsic enoyl–CoA hydratase activity", Proc Natl Acad. Sci USA, Vol 12, Mar. 1995, pp 2051–55.*

Levine, et al, "Hel–N1: an autoimmune RNA–binding protein with specificity for 3' uridylate–rich untranslated regions of growth factor mRNAs", Mol Cell Biol, vol 13, no 6, Jun. 1993, pp 3494–3504.*

Nagy, et al, "Glyceraldehyde–3–phosphate dehydrogenase selectively binds AU–rich RNA in the NAD binding region (Rossmann fold)", J of Bio Chem, Vol 270, No 6, Feb. 10, 1995, pp 2755–2763.*

Nakamaki, et al, "Characterization of adenosine–uridine–rich RNA binding factors", J of Cell Physio, Vol 165, no 3, Dec. 1995, pp484–492.*

Liu, et al, "Paraneoplastic encephalomyelitis antigens bind to the AU–rich elements of mRNA", Neurology, vol 45, 3/95, pp 544–550.*

Brewer, et al, "Poly(A) shortening and degradation of the 3' A+U –rich sequences of human c–myc mRNA in a cell–free system", Mol. and Cell. Biol, Apr. 1988, Vol 3, No. 4, pp1697–1708.*

Holcik et al. PNAS (Mar. 1997) vol. 94, pp. 2410–2414.*

Wang et al. Molec. Cell. Biol. (Mar. 1995) vol. 15 (3), pp. 1769–1777.*

Körner et al., 1998, The EMBO Journal, 17 (18):5427–5437.

Levy et al., 1996, The Journal of Biological Chemistry, 271 (5):2746–2753.

Levy et al., 1998, The Journal of Biological Chemistry, 273 (11):6417–6423.

Anderson et al., 1998, EMBO J. 17:1497–1506.

Bernstein et al., 1989, Mol. and Cell. Bio. 9:659–70.

Brewer et al., 1988, Mol. and Cell. Bio. 8:1697–1708.

Caponigro et al., 1996, Microbiol. Rev. 60:233–49.

Chen et al., 1995, Mol. and Cell. Bio. 15:5777–5788.

Colgan et al., 1997, Genes Dev. 11:2755–66.

Fan et al., 1997, Genes Dev. 11:2557–68.

Ford et al., 1999, A Companion to Methods in Enzymology 17:21–27.

Ford et al., 1999, Genes & Dev. 13:188–201.

Krikorian et al., 1991, J. Virology, 65:112–122.

Levine et al., 1993, Mol. and Cell. Bio., 13:3494–3504.

Liu et al., 1995, Neurology 45:544.

Muhlrad et al., 1994, Genes Dev. 8:855–66.

Myer et al., 1997, EMBO 16:2130–39.

(List continued on next page.)

*Primary Examiner*—Marjorie Moran
(74) *Attorney, Agent, or Firm*—Perkins Coie LLP

(57) ABSTRACT

An in vitro system is provided that recapitulates regulated mRNA stability and turnover of exogenous RNA substrates. The system comprises a cell extract optionally depleted of activity of proteins that bind polyadenylate, and a target RNA sequence. This system is used for the identification of agents capable of modulating RNA turnover, as well as agents capable of modulating RNA turnover in the presence of RNA stability modifying agents.

45 Claims, 10 Drawing Sheets

OTHER PUBLICATIONS

Nagy et al., 1995, J. Bio. Chem., 270:2755.
Nakagawa et al., 1995, PNAS USA, 92:2051–2055.
Nakamaki et al., 1995, J. Cell. Pysiology 165:484.
Presutti et al., 1995, EMBO J. 14:4022–30.
Tarun et al., 1997, EMBO J. 15:7168–77.
Weng et al., 1997, Characterization of the nonsense–mediated mRNA decay pathway and its effect on modulating translation termination and programmed frameshifting. In mRNA Metabolism and Post–Transcriptional Gene Regulation J. B. Harford, D.R. Morris, eds., Wiley–Liss, Inc., New York, pp. 241–263.
Wilson et al., 1988, Nature, 366:396–99.
Xu et al, 1997, Mol. Cell. Biol. 17:4611–21.
Zhang et al., 1993, Mol. and Cell. Bio. 13:7652–7665.
Ford et al., 1997, Mol. Cell. Biol. 17:398–406.
Ross et al., 1995, Microbiol. Reviews 59:423–50.
Caruccio et al., 1994, J Biol Chem., 269(50):31814–21, Purification of a human polyribosome–associated 3' to 5' exoribonuclease.

Chou et al., 1994, Nucleic Acids Res., 22(13):2525–31, Sequence and position requirements for uridylate–rich downstream elements of polyadenylation signals.

Karr et al., 1999, Virology, 264(1):195–204, The virion host shutoff function of herpes simplex virus degrades the 5' end of a target mRNA before the 3' end. (Abstract only).

Lee et al., 1998, J Biol Chem., 273(39):25261–71, Purification and characterization of a polysome–associated endoribonuclease that degrades c–myc mRNA in vitro.

Lu et al., 2001, J Virol, 75(3):1172–85, Herpes simplex virus virion host shutoff protein requires a mammalian factor for efficient in vitro endoribonuclease activity. (Abstract only).

Wilusz et al., 2001, Nat. Rev. Mol. Cell Biol., 2:237–46, The cap–to–tail guide to mRNA turnover.

* cited by examiner

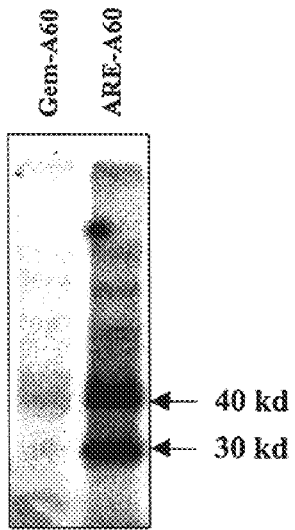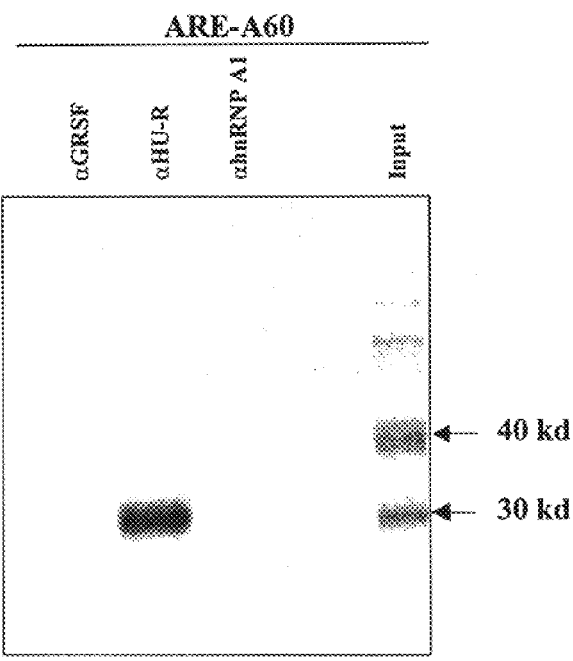

SYSTEM FOR REPRODUCING AND MODULATING STABILITY AND TURNOVER OF RNA MOLECULES

CROSS REFERENCE TO RELATED APPLICATION

This application claims benefit of Provisional Application Ser. No. 60/086,675, filed May 26, 1998.

GOVERNMENTAL SUPPORT

The research leading to the present invention was supported, at least in part, by grant No. GM56434 from the National Institutes for Health. Accordingly, the Government may have certain rights in the invention.

FIELD OF THE INVENTION

Broadly, the present invention involves a system and method for monitoring the stability of RNA and identifying agents capable of modulating RNA stability.

BACKGROUND OF THE INVENTION

The relative stability of a mRNA is an important regulator of gene expression. The half-life of a mRNA plays a role in determining both the steady state level of expression as well as the rate of inducibility of a gene product. In general, many short-lived proteins are encoded by short-lived mRNAs. Several mRNAs that encode stable proteins, such as α-globin, have also been shown to have extraordinarily long half-lives. Surveillance mechanisms are also used by the cell to identify and shorten the half-lives of mRNAs that contain nonsense codon mutations. Clearly, changes in the half-life of a mRNA can have dramatic consequences on cellular responses and function.

Little is known about mechanisms of mRNA turnover and stability in mammalian cells, but in vivo data are beginning to allow some generalizations about major pathways of mRNA turnover. The mRNA poly(A) tail can be progressively shortened throughout the lifetime of a mRNA in the cytoplasm. Controlling the rate of this deadenylation process appears to be a target for many factors that regulate mRNA stability. Once the poly(A) tail is shortened to approximately 50–100 bases, the body of the mRNA is degraded in a rapid fashion with no discernible intermediates. The process of translation also influences mRNA stability. Little is known, however, concerning the enzymes and regulatory components involved in mammalian mRNA turnover.

Several cis-acting elements have been shown to play a role in mRNA stability. Terminal (5') cap and 3'-poly(A) structures and associated proteins are likely to protect the transcript from exonucleases. Several destabilizing as well as stabilizing elements located in the body of the mRNA have also been identified. The best characterized instability element is an A-U rich sequence (ARE) found in the 3' untranslated region of many short-lived mRNAs. These AREs primarily consist of AUUUA (SEQ ID NO: 12) repeats or a related nonameric sequence. AREs have been shown to increase the rate of deadenylation and mRNA turnover in a translation-independent fashion. For example, proteins with AU-rich elements include many growth factor and cytokine mRNAs, such as c-fos, c-jun, c-myc TNFα, GMCSF, IL1–15, and IFN-β. Other stability elements include C-rich stabilizing elements, such as are found in the mRNAs of globin, collagen, lipoxygenase, and tyrosine hydroxylase. Still other mRNAs have as yet uncharacterized or poorly characterized sequence elements, for example, that have been identified by deletion analysis, e.g. VEGF mRNA.

Numerous proteins have been described that interact with some specificity with an ARE, bat their exact role in the process of mRNA turnover remains to be defined. For example, proteins which bind to the ARE described above include HuR and other ELAv family proteins, such as HuR (also called HuA), Hel-N1 (also called HuB), HuC and HuD; AUF 1 (four isoforms); tristetraprolin; AUH; TIA; TIAR; glyceraldebyde-3-phosphate; hnRNP C; hnRNP A1; AU-A; and AU-B. Many others have not been extensively characterized Through the application of genetics, the mechanisms and factors involved in the turnover of mRNA in Saccharomyces cerevisiae are beginning to be identified. One major pathway of mRNA decay involves decapping followed by the action of a 5'-to-3' exonuclease. Evidence has also been obtained for a role for 3'-to-5' exonucleases in an alternative pathway. Functionally significant interactions between the cap structure and the 3' poly(A) tail of yeast mRNAs have also been described. Several factors involved in the translation-dependent pathway of nonsense-codon-mediated decay have also been identified. Whether these observations are generally applicable to mammalian cells, however, remains to be established.

Mechanistic questions in mammalian cells are usually best approached using biochemical systems due to the inherent difficulties with mammalian cells as a genetic system. Thus, efforts have been made to develop in vitro systems to study mRNA stability and turnover. However, the presently available in vitro systems suffer from numerous limitations. For example, many suffer from poor data quality and a general lack of reproducibility that significantly limits their application. Another key problem is that most of these systems do not faithfully reproduce all aspects of mRNA stability. A significant difficulty in the development of these systems is to differentiate between random, non-specific RNA degradation and true, regulated mRNA turnover. The significance of all previous in vitro systems to the true in vivo process of mRNA stability, therefore, is unclear. To date, no in vitro mRNA stability system has been generally accepted in the field as valid and useful. Other problems that have been uncovered in presently available systems are that they usually involve a complicated extract protocol that is not generally reproducible by other laboratories in the field. Also, presently available systems can only be used to assess the stability of endogenous mRNAs, severely limiting their utility. Finally, the data quality obtained using such systems is highly variable, precluding their use in sensitive screening assays.

Accordingly, there exists a need for an in vitro RNA stability system is efficient and highly reproducible, and further, one which produces minimal to undetectable amounts of RNA degradation A further need exists for an in vitro RNA stability system wherein deadenylation of an RNA transcript in the system should occur before general degradation of the mRNA body is observed. Also needed is an in vitro RNA stability system wherein degradation of the mRNA body occurs in an apparently highly processive fashion without detectable intermediates, and further, the regulation of the rate of overall deadenylation and degradation should be observed in a sequence-specific manner. Such a system should be applicable to exogenous RNAs and allow ease of experimental manipulation.

The citation of any reference herein should not be construed as an admission that such reference is available as "Prior Art" to the instant application.

SUMMARY OF THE INVENTION

In accordance with the present invention, an in vitro system for modulating the stability and turnover of an RNA molecule is provided which models RNA processing in vivo. Thus, the present invention permits high throughput screening of compounds/macromolecules that modulate the stability of eukaryotic RNAs in order to identify and design drugs to affect the expression of selected transcripts, as well as to aid in the characterization of endogenous proteins and other macromolecules involved in mRNA stability. The in vitro system of the present invention is useful as a diagnostic aid for determining the molecular defect in selective disease alleles; development of in vitro mRNA stability systems for other eukaryotic organisms including parasites and fungi which should lead to novel drug discovery; and improving gene delivery systems by using the system to identify factors and RNA sequences that affect RNA stability.

Broadly, the present invention extends to an in vitro system capable of recapitulating regulated RNA turnover of an exogenously added preselected target RNA sequence, the system comprising a cell extract and a target RNA sequence. In a non-limiting example of the system described herein, the regulated RNA turnover is AU-rich element regulated RNA turnover or C-rich element regulated RNA turnover.

The cell extract of the system of the present invention is isolated from lysed eukaryotic cells or tissues; the cell extract may be obtained for example from a cell line, such as HeLa cells or a T cell line, but the invention is not so limited. The cell extract may be prepared from cells comprising foreign nucleic acid, such as those that are infected, stably transfected, or transiently transfected. The cell extract may be partially purified.

In one embodiment of the invention, the cell extract may be depleted of activity of proteins that bind polyadenylate. The depletion of activity of proteins that bind polyadenylate from the cell extract may be achieved by any of a number of methods, for example, the addition to the system of polyadenylate competitor RNA; the sequestration of proteins that bind polyadenylate; the addition of a proteinase that inactivates a protein that bind to polyadenylate; or addition of an agent that prevents the interaction between polyadenylate and an endogenous macromolecule that binds to polyadenylate, to name a few. As further examples of the methods for sequestration of proteins that bind polyadenylate, it may be achieved by such non-imuniting procedures as the treatment of the extract with an material that depletes macromolecules that bind polyadenylate, such as antibodies to proteins that bind polyadenylate, polyadenylate, and the combination. The material may be attached to a matrix. Other methods to achieve the depletion of the activity of proteins that bind polyadenylate may be used.

The target RNA sequence used in the system may be, by way of non-limiting examples, synthetic RNA, naturally occurring RNA, messenger RNA, chemically modified RNA, or RNA-DNA derivatives. The target RNA sequence may have a 5' cap and a 3' polyadenylate sequence. The target RNA sequence may be unlabeled target RNA sequence, labeled target RNA sequence, or a the combination of both. The labeled RNA sequence may be labeled with a moiety such as, but not limited to a fluorescent moiety, a visible moiety, a radioactive moiety, a ligand, and a combination of fluorescent and quenching moieties. Other moieties and means for labeling RNA are embraced herein.

The system of the present invention may additionally include exogenously added nucleotide triphosphate; ATP is preferred. It may also include a reaction enhancer to enhance the interaction between the various components present in the system, for example, polymers such as but not limited to polyvinyl alcohol, polyvinylpyrrolidone and dextran; polyvinyl alcohol is preferred.

The present invention is also directed to a method for identifying agents capable of modulating the stability of a target RNA sequence. The method is carried out by preparing the system described above which includes the cell extract depleted of activity of proteins that bind polyadenylate and the target RNA sequence; introducing into the aforesaid system an agent to be tested; determining the extent of turnover of the target RNA sequence by, for example, determining the extent of degradation of the labeled target RNA; and then identifying an agent which is able to modulate the extent of RNA turnover as capable of modulating the stability of the target RNA sequence.

The method described above may additionally include nucleotide triphosphate, ATP being preferred. The agent to be tested may be, but is not limited to, an RNA stability modifying molecule. The non-limiting selection of the types of target RNA sequence and the non-limiting types of labels useful for the RNA as described hereinabove.

The method of the present invention is useful for identifying agents which can either increase or decrease the stability of said target RNA sequence. Such agents may be capable of modulating the activity of an RNA binding molecule such as, but not limited to, C-rich element binding proteins and AU rich element binding proteins, examples of the latter including HuR and other ELAv family proteins, such as HuR, Hel-N1, HuC and HuD; AU1 1; tristetraprolin; AUH; TIA; TIAR; glyceraldehyde-3-phosphate; hnRNP C; hnRNP A1; AU-A; and AU-B. This list is provided as illustrative of the types of molecules that may be evaluated in the present invention, but is by no means limiting.

In a further embodiment of the present invention, a method is provided for identifying an agent that is capable of modulating the stability of a target RNA sequence in the presence of an exogenously added RNA stability modifier or RNA binding macromolecule. Non-limiting examples of such molecules are described above. The method is carried out by preparing the system described above which includes the cell extract can be depleted of activity of proteins that bind polyadenylate and the target RNA sequence; introducing into the aforesaid system the exogenously added RNA stability modifier or binding macromolecule and the agent to be tested; determining the extent of turnover of the target RNA sequence by, for example, determining the extent of degradation of the labeled target RNA; and then identifying an agent able to modulating the extent of the RNA turnover as capable of modulating the stability of the target RNA sequence in the presence of the exogenously added RNA stability modifier.

The non-limiting selection of the components of this method are as described above. The aforementioned method is useful, for example, when the RNA stability modifier decreases the stability of said target RNA sequence, and the agent to be identified increases the stability of the target RNA sequence that is decreased by the RNA stability modifier in addition, the method is useful when the RNA stability modifier increases the stability of the target RNA sequence, and the agent to be identified decreases the stability of the target RNA sequence that is increased by the RNA stability modifier. Non-limiting examples of RNA stability modifiers include C-rich element binding proteins, and AU rich element binding proteins, examples of AU rich element binding proteins, including HuR and other ELAv family proteins, such as HuR, Hel-N1, HuC and HuD; AUF1; tristetraprolin; AUH; TIA; TIAR; glyceraldehyde-3-phosphate; hnRNP C; hnRNP A1; AU-A; and AU-B. This list is provided as illustrative of the types of molecules that may be evaluated in the present invention, but is by no means limiting.

The present invention is further directed to a method for identifying an agent capable of modulating the deadenylation of a target RNA sequence comprising preparing the system described above in the absence of nucleotide triphosphate, such as ATP; introducing an agent into the system; and monitoring the deadenylation of the target RNA sequence. Furthermore, the invention is also directed towards a method for identifying an agent capable of modulating the deadenylation and degradation of a target RNA sequence comprising preparing the system described herein in the presence of ATP; introducing the agent into the system; and monitoring the deadenylation and degradation of the target RNA sequence. These embodiments may also be carried out in the presence of an RNA stability modifier or RNA binding macromolecule to determine the ability of the agent to modulate the effect of the modulator or binding molecule on RNA stability.

It is a further aspect of the present invention to provide a method for identifying an agent capable of modulating cell growth or cell differentiation in a mammal comprising determining the ability of said agent to modulate the stability of a target RNA sequence involved in the modulation of cell growth or differentiation in accordance with the methods described above. The agents capable of modulating cell growth or cell differentiation may intervene in such physiological processes as cellular transformation and immune dysregulation, but the invention is not so limiting.

It is yet a further aspect of the present invention to provide a method for identifying, characterizing and isolating an endogenous molecule suspected of participating in the deadenylation or degradation of RNA or regulation thereof comprising preparing the system described hereinabove; introducing a protein suspected of participating in the regulation of RNA turnover into said system; and monitoring the stability of the target RNA sequence. The endogenous molecule suspected of participating in the deadenylation and/or degradation of RNA or regulation may be protein or RNA.

In another embodiment of the invention, a method is provided for identifying an agent capable of modulating the degradation a target RNA sequence in the absence of deadenylation comprising providing a cell extract in the presence of a nucleotide triphosphate; introducing said agent into said cell extract; and monitoring the degradation of said target RNA sequence in said extract.

A further aspect of the present invention is directed to a kit for monitoring the stability of a preselected target RNA sequence under conditions capable of recapitulating regulated RNA turnover. The kit comprises a cell extract that optionally may be depleted of activity of proteins that bind polyadenylate; other reagents; and directions for use. The kit may further comprise nucleotide triphospliates, a reaction enhancer, or both.

Accordingly, it is an object of the invention to provide a system for modulating the stability and turnover of an RNA molecule in vitro, which permits a skilled artisan to study the turnover generally, or deadenylation and degradation specifically, of an RNA transcript, and screen drugs which can modulate the stability and turnover of an RNA tran-script. The turnover may be in the absence or presence of exogenously added RNA stability modulators, or permit the study of the role of endogenous molecules in RNA turnover.

It is another embodiment of the invention to provide a kit that a skilled artisan can readily use to modulate the stability and turnover of an RNA molecule in vitro, and investigate the aforementioned agents.

These and other aspects of the present invention will be better appreciated by reference to the following drawings and Detailed Description.

BRIEF DESCRIPTION OF THE DRAWINGS

FIG. 1A Poly(A) competitor RNA activates nucleolytic activities in the extract. A capped, radiolabeled 54 base RNA containing a 60 base poly(A) tail (Gem-A60) was incubated at 30° C. with S100 extract in the absence (lanes marked S100) or presence (Lanes marked S100+Poly(A)) of 500 ng of cold poly(A) RNA as described in Materials and Methods of Example 1 for the times indicated. RNA products were analyzed on a 5% acrylamide gel containing 7M urea. The position of a deadenylated, 54 base transcript (Gem-A0) is indicated on the right. FIG. 1B. The shortening of input transcripts is due to a 3'-to-5' exonuclease. Gem-A60 RNA, labeled exclusively at the 5' cap, was incubated in the in vitro mRNA stability system for the times indicated. Reaction products were analyzed on a 5% acrylamide gel containing 7M urea. The position of a deadenylated, 54 base transcript (Gem-A0) is indicated on the right. FIG. 1C. An alternative approach also demonstrates that the shortening of input transcripts is due to a 3'-to-5' exonuclease. ARE-A60 RNA, radiolabeled at A residues, was incubated in the in vitro stability system for the times indicated. Reaction products were hybridized to a DNA oligo and cleaved into 5' and 3' fragments using RNase H. Fragments were analyzed on a 5% acrylamide gel containing 7M urea. FIG. 1D. The 3'-to-5' exonuclease activity is a specific deadenylase. Geii-Aq60 RNA or a variant that contains 18 extra nucleotides after the poly(A) tract (Gem-A60- 15) were incubated in the in vitro stability system for the times indicated. RNA products were analyzed on a 5% acrylamide gel containing 7M urea. The position of a deadenylated, 54 base transcript (Gem-A0) is indicated on the left. 31±11.0% of the input Gem-A60 RNA was deadenylated/degraded in 30 min.

FIG. 2A. AU-rich elements dramatically increase the rate of turnover in the in vitro system. Gem-A60 RNA or a polyadenylated transcript that contains the 34 base AU-rich element from the TNF-α mRNA, were incubated in the in vitro stability system for the times indicated. RNA products were analyzed on a 5% acrylamide gel containing 7M urea. The positions of deadenylated transcripts (Gem-A0 and ARE-A0) are indicated.. The ARE-A60 RNA was deadenylated/degraded 6.6±0.4 fold faster than Gem-A60 RNA. FIG. 2B. The AU-rich element from c-fos mRNA also functions as an instability element in vitro. Gem-A60 RNA or a transcript that contains the 72 base AU-rich element from the c-fos mRNA (Fos-A60) were incubated in the in vitro stability system for the times indicated. RNA products were analyzed on a 5% acrylamide gel containing 7M urea. The positions of deadenylated transcripts (Gem-A0 and Fos-A0) are indicated. The Fos-A60 RNA was deadenylated/degraded 3.5±0.3 fold faster than Gem-A60 RNA. FIG. 2C. The ability of AU-rich elements to mediate transcript instability in the in vitro system is sequence-specific. ARE-A60 RNA or a variant that contains a mutation at every fourth position (mt ARE-A60; see Materials and Methods) were incubated in the in vitro stability system for the times indicated. RNA products were analyzed on a 5% acrylamide gel containing 7M urea. The positions of deadenylated transcripts (ARE-A0 and mt ARE-A0) are indicated. Mutations in the ARE reduced the rate of deadenylation/degradation by 3.7±1.4 fold compared to the wild type ARE-A60 transcript. FIG. 2D. The TNF-α AU-rich element mediates instability in a heterologous context. A polyadenylated 250 base RNA derived from the SV late transcription unit (SV-A60), or a variant that contains the 34 base AU-rich element from the TNF-α mRNA (SVARE-A60), were incubated in the in vitro stability system for the times indicated. RNA products were analyzed on a 5% acrylamide gel containing 7M urea. The positions of deadenylated transcripts (SV-A0 and SVARE-A0) are indicated. SVARE-A60 RNA was deadenylated/degraded 3.5±0.7 fold faster than SV-A60 RNA. FIG. 2E. The AU-rich element derived from the GM-CSF mRNA functions in vitro on nearly a full length RNA substrate. A nearly full length version of the GM-CSF mRNA that contained an AU-rich element (GM-CSF(+ARE), or a version in which the AU-rich element was deleted (GM-CSF(-ARE), were incubated in the in vitro stability system for the times indicated. RNA products were analyzed on a 5% acrylamide gel containing 7M urea. GM-CSF(+ARE) was deadenylated/degraded 2.8+0.2 fold faster than the GM-CSF (-ARE) transcript. FIG. 3A. Degradation, but not deadenylation, requires ATP. SV-ARE-A60 RNA was incubated in the in vitro system in the presence ((+) ATP lanes) or absence ((–) ATP lanes) for the times indicated. RNA products were analyzed on a 5% acrylamide gel containing 7M urea. The positions of the deadenylated SVARE-A) transcript is indicated. FIG. 3B. AU-rich elements regulate the rate of deadenylation on RNA substrates which carry a physiologic length poly(A) tail. SV RNA or SV-ARE RNA (a variant that contains an AU-rich element) were polyadenylated with yeast poly(A) polymerase and species that contained tails of approximately 150–200 bases were gel purified. These RNAs (SV(A 150–200) and SVARE(A 150–200) were incubated in the in vitro stability system for the times indicated. RNA products were analyzed on a 5% acrylamide gel containing 7M urea. The positions of deadenylated transcripts (SV-A0 and SVARE-A0) are indicated. SVARE(A 150–200) RNA was deadenylated 2.2+0.3% fold faster than the SV(A 150–200) transcript.

FIGS. 4A–B: The HuR protein of the ELAV family specifically binds to the TNF-α AU-rich element in the in vitro system. FIG. 4A. Two proteins specifically interact with the TNF-α AU-rich element. Gem-A60 and ARE-A60 RNAs were radiolabeled at U residues and incubated in the in vitro stability system for 5 min in the presence of EDTA (to block degradation and allow for accurate comparisons). Reaction mixtures were irradiated with UV light, cleaved with RNase A, and protein-RNA complexes were analyzed on a 10% acrylamide gel containing SDS. The approximate sizes of the cross linked proteins indicated on the right were deduced from molecular weight markers. FIG. 4B. The 30 kDa protein is HuR. Radiolabeled ARE-A60 RNA was incubated in the in vitro RNA stability system and cross-linked to associated proteins as described above. Cross linked proteins were immunoprecipitated using the indicated antisera prior to analysis on a 10% acrylamide gel containing SDS. The lane marked Input denotes total cross linked proteins prior to immunoprecipitation analysis.

FIG. 5A. Competition analysis suggests that AU-rich element binding factors are required for deadenylation and degradation of transcripts. SVARE-A60 RNA was incubated in the in vitro stability system for 30 min. in the presence of the indicated amounts of a synthetic RNA competitor that contained the TNF-α AU-rich element (ARE comp.) or a non-specific sequence. RNA products were analyzed on a 5% acrylamide gel containing 7M urea. The position of deadenylated SVARE-A0 RNA is indicated. FIG. 5B. Reaction mixtures were prepared as described in panel A with the addition of EDTA to inhibit RNA turnover. Protein-RNA interactions were analyzed by UV cross linking analysis and analyzed on a 10% acrylamide gel containing SDS. The positions of AU rich element-specific cross linked species is indicated on the left. FIG. 5C. Reactions were prepared exactly as described for Panel B, except samples were inmunoprecipitated using a-HuR specific antisera prior to gel electrophoresis.

FIG. 6A. SVARE-A60 RNA was incubated ii the in vitro system in the presence (lanes (+) Hel-N 1)) or the absence (lanes (–) Hel-N1) of 1 ug of recombinant Hel-N1 protein. RNA products were analyzed on a 5% acrylamide gel containing 7M urea. The position of deadenylated SVARE-A0 transcript is indicated. FIG. 6B. SVARE-A60 RNA was incubated in the in vitro system in the presence of 1 ug of recombinant Hel-N1 (lanes (+) Hel-N1), GST only (lanes (+) GST), or an unrelated RNA binding protein hnRNP H' (lanes (+) hnRNP H'). RNA products were analyzed on a 5% acrylamide gel containing 7M urea. The position of deadenylated SVARE-A0 transcript is indicated. FIG. 6C. ARE-A60 RNA, or an unrelated transcript that lacked an AU-rich element (CX-A60), were incubated in the in vitro stability system for 30 min. in the presence (+lanes) or absence (–lanes) of~1 ug of Hel-N2 protein. RNA products were analyzed on a 5% acrylamide gel containing 7M urea. The positions of deadenylated transcripts are indicated. FIG. 6D. A variant of SV-A60 RNA that contained the TNF-α ARE in the 5' portion of the transcript (SV5' AGE-A60) was incubated in the in vitro system for 50 min. in the absence (–lane) or presence (+lane) of 1 μg of Hel-N2 protein. RNA products were analyzed on a 5% acrylamide gel containing 7 M urea. The positions of imput and deadenylated transcripts are indicated.

DETAILED DESCRIPTION OF THE INVENTION

Figure 1A:
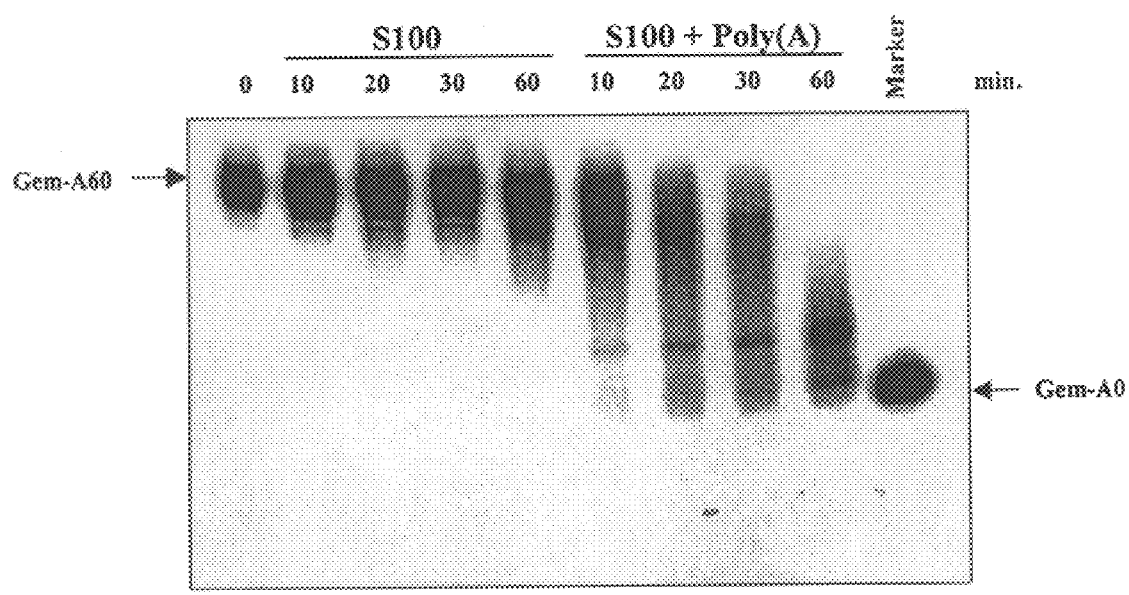
FIGS. 1A–D: The addition of poly(A) tocytoplasmic S100 extracts activates specific deadenylase and degradation activities.

Numerous terms and phrases are used throughout the instant Specification. The meanings of these terms and phrases are set forth below.

In particular, as used herein "half-life" of an RNA molecule refers to the measurement of the decline in the amount of an RNA molecule to serve as a template for the synthesis of its protein product.

As used herein "turnover" refers to the degradation of an RNA molecule. Turnover comprises deadenylation and degradation.

As used herein a "cap" or "5' cap" or "terminal cap", and be used interchangeable, and refer to a 7-methyl guanosine (7mG) cap chemically conjugated to the most 5' nucleotide of the RNA molecule.

As used herein, the phrase "polyadenylic acid (poly(A)) tail" refers to a string of contiguous adenylic acids (polyadenylate) added post transcriptionally to the 3' end of an RNA molecule, such as mRNA.

As used herein, the tern "stability" refers to the maintenance of an RNA molecule so that it can function, and thus retard the degradation process of an RNA molecule.

As used herein, the phrase "a polyadenylic acid competitor nucleic acid oligomer" refers to an oligomer comprising contiguous adenylic acids" which can be added to a system of the invention and sequester proteins that bind poly(A). Thus, the degradation of a particular RNA molecule having a poly(A) tail can be modulated.

Also, as used herein, the phrase "restriction endonuclease" refers to an enzyme that recognizes specific nucleotide sequences in a nucleic acid molecule, and produces a double-stranded break within or near the site. Some restriction enzymes, such as EcoRI or HindIII produce "complementary tails" on each of fragments produced. These tails are said to be "sticky" because under hybridization conditions they can reanneal with each other. Thus, if two separate nucleic acid molecules share the same restriction site, then both will contain complementary single-stranded tails when treated with the same restriction endonuclease, and can be spliced together forming a recombinant nucleic acid molecule.

Naturally, as used herein, the phrase "restriction endonuclease site" refers to a specific nucleotide sequence that is recognized by a specific restriction endonuclease.

Furthermore, numerous conventional molecular biology, microbiology, and recombinant DNA techniques within the skill of the art can be readily utilized to practice the instant invention. Such techniques are explained fully in the literature. See, e.g., Sambrook, Fritsch & Maniatis, *Molecular Cloning: A Laboratory Manual*, Second Edition (1 989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication uinder its own control.

A "cassette" refers to a segment of a nucleic acid molelcule, such as DNA or RNA, that can be inserted into a vector at specific restriction sites. The segment of the nucleic acid molelcule may encode a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation. A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

The present invention is based upon Applicant's discovery of a heretofore unknown system for activating regulated turnover of RNA molecules in vitro that surprisingly and unexpectedly permits a skilled artisan to study and to modulate the stability and thus the turnover of a RNA molecule in vitro. Thus, the new and useful system of the invention permits accurate and faithful reproduction of both general and regulated aspects deadenylation and degradation of an RNA molecule, also referred to herein as recapitulating regulated RNA turnover, particularly a eukaryotic mRNA transcript. In particular, the new and useful system of the invention permits minimal amounts, preferably undetectable, of mRNA turnover, and. further, deadenylationi of an RNA molecule occurs in the system prior to degradation of the RNA molecule, which mimics the turnover process of RNA found in vivo.

The key to the development of the system and methods utilizing the system are based on the discovery that polyadenylate competitor RNA is capable of sequestering proteins that bind polyadenylate and consequently activating the deadenylase enzyme, inducing RNA turnover. As it was heretofore considered that such proteins that bind polyadenylate may contribute to RNA deadenylation, the present finding that such proteins are, in contrast, stabilizers of RNA, led to the realization that sucb proteins are interacting with and inactivating destabilizing mediators in vivo. Thus, the present invention is directed to an in viLro system capable of recapitulating regulated RNA turnover of an exogenously added preselected target RNA sequence comprising a cell extract depleted of activity of proteins that bind polyadenylate, and a preselected target RNA sequence. In one particular embodiment, the regulated RNA turnover is that modulated by AU-rich element (ARE) regulated RNA turnover. Examples of mRNAs with AU-rich elements include those of, by way of non-limiting example, c-fos; c jun; C-myc TNF-α, GMCSF, IL1–15, and IFN-β. As noted above, AU-rich elements are sites for binding of numerous proteins, including the ELAV family of ARE-binding proteins, such as HuR, He1-N1, HuC and HuD; others include AUF1; tristetraprolin; AUH; TIA; TIAR; glyceraldehyde-3-phosphate; hnRNP C; hnRNP A1; AU-A; and AU-B. In another embodiment, the regulated RNA turnover is that modulated by C-rich element (CRE) regulated RNA turnover, such elements as found in the mRNA of globin mRNAs, collagen, lipoxygenase, and tyrosine hydroxylase. Another mRNA with an as yet uncharacterized sequence element is that of VEGF. The invention, however, is not so limiting as to the particular elements or binding proteins to these elements involved in the regulation of RNA turnover.

The cell extract of the present invention is prepared from lysed eukaryotic cells or tissues. Various methods known to the skilled artisan may be used to prepare the cell extract. Various sources of cells may be used, including fresh cells and tissues, and cells lines. Such cells may comprise foreign nucleic acid, such as in cells that are infected; or are transiently or stably transfected with a mammalian expression vector, the latter as described in more detail below. For certain purposes, for example to investigate the role of infection, and in particular intracellular infection, on RNA turnover, infected cells may be utilized as the source of the cell extract herein. Cells infected with viruses or other intracellular microorganisms such as Listeria monocytogenes, HTLV, herpes simplex virus, and HIV, may be employed for these particular circumstances. Furthermore, prior to preparation of the cell extract, cells may be exposed to certain chemical or other extracellular stimuli, for example, hormones, growth factors, and kinase and phosphatase inhibitors, which may alter RNA turnover, for which subsequent studies as described herein may be used to identify the induction of certain proteins involved in modulating RNA turnover, or for the identification of agents which may counteract adverse RNA turnover modulation induced by such stimuli. As will be noted in more detail below, the methods herein may be used to identify agents which may protect cells by interfering with adverse RNA turnover induced by various sources. The cell extract is preferably free of nuclei and nuclear contents and comprises cytoplasm, but this is not essential unless particular components, such as enzymes or other factors, from nuclei, interfere with the operation of the system. In a typical preparation, which may be modified without departing from the scope of the invention, cells are grown, harvested, lysed, centrifuged for 100,000×g for 1 hour, and dialyzed. Glycerol may be added to protect the extract if stored frozen.

As described above, a cell used to prepare the cell extract may comprise foreign DNA. An isolated nucleic acid molecule to placed in a system of the invention can initially be inserted into a cloning vector to produce numerous copies of the molecule. A large number of vector-host systems known in the art may be used. Possible vectors include, but are not limited to, plasmids or modified viruses, but the vector system must be compatible with the host cell used. Examples of vectors include, but are not limited to, E. coli, bacteriophages such as lambda derivatives, or plasmids such as pBR322 derivatives or pUC plasmid derivatives, e.g., pGEX vectors, pmal-c, pFLAG, etc. Thie insertion into a cloning vector can, for example, be accomplished by ligating the nucleic acid molecule into a cloning vector which has complementary cohesive termini. However, if the complementary restriction sites used to fragment the nucleic acid molecule are not present in the cloning vector, the ends of the molecule may be enzymatically modified. Alternatively, any site desired may be produced by ligating nucleotide sequences (linkers) onto the termini of the nucleic acid molecule; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the nucleic acid molecule are generated. Preferably, the cloned nucleic acid molecule is contained on a shuttle vector plasmid, which provides for expansion in a cloning cell, e.g., E. coli, and facile purification for subsequent insertion into an appropriate expression cell line, if such is desired. For example, a shuttle vector, which is a vector that can replicate in more than one type of organism, can be prepared for replication in both E. coli and Saccharomyces cerevisiae by linking sequences from an E. coli plasmid with sequences from the yeast 2μ plasmid.

Naturally, any of the methods previously described for the insertion of an isolated nucleic acid molecule into a cloning vector may be used to construct expression vectors containing a nucleic acid molecule consisting of appropriate transcriptional/translational control signals and the protein coding sequences. These methods may include in vitro recombinant DNA and synthetic techniques and in vivo recombination (genetic recombination).

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (Pstl, Sall, Sbal, Smal, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE 14 (HindIII, XbaI, Smal, Sbal, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamHI, SfiI, XhoI, NotI, NheI, HindIII, NheI, PvuII, and KpnI cloning site, constitutive RSV-LTR promoter, hygromycin selectable marker; Invitrogen), pCEP4 (BamHI , SfiI, XhoI, NotI, NheI, HindIII, NheI, PvuII, and KpnI cloning site, constitutive hCMV immediate early gene, hygromycin selectable, marker; Invitrogen), pMEP4 (KpnI, PvuI, NheI, HindIII, NotI, XhoI, SfiI, BamHI cloning site, inducible metallothionein IIa gene promoter, hygromycin selectable marker: Invitrogen), pREP8 (BamHI, AhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (Hindail, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601(SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Once a particular nucleic acid molecule, such as RNA, is inserted into a vector, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few. In addition, a host cell strain may be chosen which modulates the expression of the inserted sequences, or modifies and processes the gene product in the specific fashion desired.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Cells useful for the preparation described herein include immortalized or partially immortalized cells which can be grown in large amounts under defined conditions, such as HeLa cells and various T-cell cell lines. Other sources include tissues, blood cells, or myeloid cells. Other sources are well within the realm of the present invention.

The cell extract of the system described herein is depleted of activity of proteins that bind polyadenylate. This may be achieved by any one or a combination of methods such as the following. While not being bound by theory, each of these methods either removes the proteins that bind polyadenylate, or inactivate the binding activity. These procedures may be applied to the cell extract as it is used in the methods described herein, or the cell extract may be treated beforehand. For example, a polyadenylate competitor RNA may be added to the cell extract to provide an irrelevant RNA sequence to which the binding proteins may bind, thus clearing the target RNA sequence of such binding proteins. In another embodiment, sequestration of proteins that bind polyadenylate may be performed. Sequestration may be achieved by adding to the cell extract or exposing the cell extract to a material that binds the aforementioned proteins, such as antibodies to proteins that bind polyadenylate, or polyadenylate sequences themselves or macromolecules comprising polyadenylate sequences which serve as binding targets for such proteins. Alternatively or in addition, these protein binding materials may be bound to a matrix, such as agarose beads, and the cell extract passed through a column of such beads to remove the proteins which bind polyadenylate. The preparation of such beads covalently modified to comprise antibodies or RNA sequences, whether polyadenylate or sequences comprising polyadenylate, are known to the skilled artisan. Another means for reducing or eliminating such activity from the cell extract is by exposure to one or more proteinase known to inactivate a protein that bind to polyadenylate. These proteinases may be added to the extract, or bound to a matrix and exposed to the extract, after which inactivation the beads may be removed. A further means encompasses addition to the extract of an agent that prevents the interaction between polyadenylate and an endogenous macromolecule that binds to polyadenylate. These and other methods embraced by the present invention achieve the desired goal of depleting macromolecules that bind polyadenylate from the cell extract, thus allowing the cell extract in combination with the target RNA sequence to undergo in vivo-like RNA turnover. One or a combination of the aforesaid methods may be employed to reduce the level of such protein to an acceptable limit, dependent upon the source of the cells or tissues from which the extract is made, the particular target RNA sequence, and other factors. As will be noted below, certain macromolecules that bind to polyadenylate may be included in particular screening assays or other methods employing the system and methods described herein when that particular protein or other macromolecule is subject to investigation as described herein.

In a further embodiment of the invention, the cell extract may be partially purified or otherwise manipulated. For example, the cell extract may be partially purified to remove certain components before being placed in the system of the invention, before or after being optionally depleted of macromolecules that bind polyadenylate. For example, certain non-specific factors and/or activities unrelated to of interfering with the methods of the present invention may be removed from the cell extract. The skilled artisan will recognize for the particular target RNA being investigated hereunder the need for partial purification of the extract and the need for depletion of factors that bind polyadenylate. Furthermore, other components may be added to ensure that the system of the invention recapitulates regulated RNA turnover.

The target RNA sequence in the system of the present invention may be an one of a number of RNA or modified RNA molecules. For example, synthetic RNA may be prepared by solid phase synthesis, or reproduced by in vitro transcription using phage polyiherase as is known to the skilled artisan. Naturally occurring RNA may be isolated from cells, tissues, and other biological sources. The RNA may be a messenger RNA (mRNA), a preferred species herein, or RNA-DNA derivatives. Messenger RNA typically comprises a 5' cap and a 3' polyadenylate sequence. Chemically modified RNA, such as RNA modified by phosphothioate moiety(ies), is embraced herein.

The particular RNA, including mRNA, used in the system and methods of the present invention may be selected depending on the particular species of mRNA to be studied. Investigations of mRNA turnover, endogenous modulators of its turnover and exogenously added molecules, particularly small molecules which affect mRNA turnover, have important therapeutic implications in the prophylaxis and treatment of a variety of conditions and diseases. Certain mRNAs are short-lived, such as those of cytokines; others are long-lived, such as globin message. The regulation of mRNA lifetimes for particular proteins and particular cell types may be subject to various adverse effects, from infection to external stimuli, which alter the turnover and hence cellular physiology. In various conditions, altered expression of cellular proteins and cellular phenotypes may be consequences of altered mRNA turnover. Pharmacological intervention of such altered mRNA turnover, to restore an altered turnover, or the induction of an altered turnover to achieve a benefit to the organism, are achievable based upon the systems and methods described herein. For example, a particular mRNA, such as that of the proinflammatory cytokine TNFα, is selected as a target for identification of small molecule modulators that may decrease the turnover, and this prolong the lifetime, and expression, of this protein by inflammatory cells. Such modulators may provide substantial benefit in the treatment of certain immunological diseases wherein an increased secretion of TNFα is beneficial. Conversely, massive overproduction of TNFα in sepsis, or its adverse effects in rheumatoid arthritis and inflammatory bowel disease may be ameliorated by use of an agent which further increases the turnover and thus decreases the expression of TNFα by inflammatory cells.

The application of the invention herein to other mRNA species is embraced by the teachings herein. In particular, the methods of the present invention facilitate high throughput screening for the identification of modulators of RNA turnover, to be applied to the treatment or prophylaxis of disease.

One aspect of the system and method of the present invention is monitoring the turnover of the target RNA sequence. This may be achieved by any one or a combination of various methods known to the skilled artisan, one of which is the provision of labeled RNA. The target RNA sequence of the present may be unlabeled, labeled, or a combination. For example, after setting up conditions under which the deadenylation and/or degradation of the unlabeled target RNA sequence occurs, its level may be assessed by any of a number of methods utilizing a labeled probe, such as by hybridization, or by way of UV absorbance, gel electrophoresis followed by specific or nonspecific staining, or using an amplification system, such as phage polymerase, and then quantitation by a suitable amplification-based technique such as the molecular beacon method. Alternatively, and perhaps more simply, the target mRNA sequence may be labeled, and the extent of intact sequence or degraded RNA fragments readily quantitated. Labels such as a fluorescent moiety, a visible moiety, a radioactive moiety, a ligand, and a combination of fluorescent and quenching moieties. These non-limiting examples are provided for purposes of illustration only.

Furthermore, optionally, an RNA molecule or a portion thereof, such as its poly(A) tail, may be detectably labeled using routine protocols readily known to a skilled artisan. Suitable labels include enzymes, fluorophores (e.g., fluorescein isothiocyanate (FITC), phycoerythrin (PE), Texas red (TR), rhodamine, free or chelated lantlianide series salts, especially $Eu^{3+}$, to name a few fluorophores), chromophores, radioisotopes, chelating agents, dyes, colloidal gold, latex particles, ligands (e.g., biotin), and chemiluininescent agents. When a control marker is employed, the same or different labels may be used for the receptor and control marker.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. Particular ribonucleotides bay be prepared using the appropriate isotopes, and the labeled RNA prepared by solid phase synthesis. Alternatively, moieties comprising the isotopes may be covalently bound to the RNA. In the instance where the label is an enzyme, detection may be accomplished by any of the presently utilized colorimetric, spectrophotometric, fluorospectrophotometric, amperomnetric or gasometric techniques known in the art. In a further example, biotin moieties may be incorporated into the RNA by any number of means. Subsequently, the biotinylated RNA or degradation fragments may be quantitated by an avid in reagent.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No 4,857,453.

Suitable enzymes include, but are not limited to, alkaline phosphatase and horseradish peroxidase. Other labels for use in the invention include magnetic beads or magnetic resonance imaging labels.

As noted herein, turnover of RNA occurs in two steps: deadenylation, which is not dependent upon the presence of nucleotide triphosphates, and degradation, which is so dependent. The level of nucleoside tripphosphates, including ribonucleotide and/or deoxyribonucleotide triphosphates, ATP, UTP, CTP, TTP, and/or GTP, in the cell extract may or may not be sufficient to permit the degradation aspect of RNA turnover to occur. In one embodiment of the present invention, the system described herein additionally comprises exogenously added nucleotide triphosphate, preferably ATP.

It was noted during the development of the present invention that the inclusion of a reaction enhancer resulted in a slight stimulation in the efficiency of RNA degradation. This is likely to be due to its ability to promote macromolecular complex formation in vitro. Therefore, the invention herein optionally includes the use of a reaction enhancer such as a polymer, to stimulate interaction among the components of the system. Non-limiting examples include polyvinyl alcohol, polyvinylpyrrolidone and dextran; polyvinyl alcohol is preferred.

The above-described system which recapitulates in vitro the RNA turnover of preselected RNA sequences has several utilities, in particular, the identification of the role of endogenous factors and exogenous modulators in RNA turnover. The present invention is broadly directed to a method for identifying an agent capable of modulating the stability of a target RNA sequence comprising (A) preparing the system as described hereinabove;
(B) introducing said agent into said system;
(C) determining the extent of turnover of said target RNA sequence; and
(D) identifying an agent able to modulate the extent of said turnover as capable of modulating the stability of said target RNA sequence.

The above method may additionally comprise added nucleotide triphosphate, preferably ATP, for the purposes described above.

Agents whose activity in modulating RNA turnover may de detected in the aforementioned method include but is not limited to an RNA stability modifying molecule.

As described above, the target RNA sequence may be selected as described above, depending on the particular RNA to be studied. The target RNA may be unlabeled target RNA sequence, labeled target RNA sequence, or the combination thereof. Labels include but are not limited to a fluorescent moiety, a visible moiety, a radioactive moiety, a ligand, or a combination of fluorescent and quenching moieties.

The monitoring the extent of turnover of said target RNA sequence comprises determining the extent of degradation of said labeled target RNA, by the methods described above.

In particular, the present method may be directed to identifying agents capable of modulating the stability of a target RNA sequence which increases the stability of the target RNA sequence, or alternatively, decreasing the stability of the RNA sequence.

In a particular embodiment, the agent is capable of modulating the activity of a AU rich element binding protein or a C-rich element, but it is not so limited. Examples of AU rich element binding proteins and C-rich element binding proteins are as described herein.

In a further embodiment of the present invention, a method is provided for identifying an agent capable of modulating the stability of a target RNA sequence in the presence of an exogenously added RNA stability modifier comprising (a) preparing the system as described hereinabove;
(b) introducing said RNA stability modifier into said system;
(c) introducing said agent into said system;
(d) determining the extent of turnover of said target RNA sequence; and
(e) identifying an agent able to modulate the extent of said turnover as capable of modulating the stability of said target RNA sequence in the presence of said exogenously added RNA stability modifier.

This aspect of the invention is directed to identifying agents, in particular small molecules, capable of affecting the activity of a RNA turnover modulator. As described above, such small molecules may be screened to determine their effect on the RNA stabilizing or destabilizing ability of an endogenous mediator, which is added to the test system. Alternatively, it may be used to identify compounds which agonize or antagonize exogenous agents. The components of the system, including nucleotide triphosphate, the target RNA, labels, are as described above. In one aspect of this embodiment, the RNA stability modifier increases the stability of said target RNA sequence, and in a further embodiment, the agent decreases the stability of said target RNA sequence increased by said RNA stability modifier. In another embodiment, the RNA stability modifier decreases the stability of said target RNA sequence, and in a further embodiment, the agent increases the stability of said target RNA sequence decreased by said RNA stability modifier.

Candidate series of RNA stability modifiers include the AU rich element binding proteins, but the invention is not limited to such factors. Examples of known proteins having such elements in the mRNA, and binding proteins to the elements, are described above, however, the invention is not limited to these examples.

Furthermore, in another embodiment, the macromolecules that bind RNA that are removed from the cell extract in accordance with the aforementioned procedures may be added back to the system herein to investigate their role in RNA turnover as well as the effect of agents, in particular small molecules, on RNA turnover modulated by these macromolecules that bind RNA. This embodiment may be applied to any of the methods described herein. In yet another embodiment, the target RNA may be loaded with a macromolecule that binds RNA prior to addition to the system herein, for the same purposes stated above.

As noted above, the cell extract used in any of the methods described herein may be partially purified.

A method is also provided for identifying an agent capable of modulating the deadenylation of a target RNA sequence comprising (A) preparing the system of the present invention in the absence of a nucleotide triphosphate;
(B) introducing said agent into said system; and
(C) monitoring the deadenylation of said target RNA sequence in said system.

A further method is provided for identifying an agent capable of modulating the deadenylation and degradation of a target RNA sequence comprising (A) preparing the system of the present invention in the presence of ATP;
(B) introducing said agent into said system; and
(C) monitoring the deadenylation and degradation of said target RNA sequence in said system.

Method are also provided herein for identifying an agent capable of modulating cell growth or cell differentiation in a mammal comprising determining the ability of said agent to modulate the stability of a target RNA sequence involved in the modulation of cell growth or differentiation, utilizing the aforementioned methods. The agent capable of modulating cell growth or cell differentiation may intervene in cellular transformation, or in immune dysregulation.

A further embodiment of the present invention is directed to a method for identifying, characterizing or isolating an endogenous molecule suspected of participating in the deadenylation or degradation of RNA or regulation thereof comprising (A) providing the system of the present invention as described above;
(B) introducing said protein suspected of participating in the regulation of RNA turnover into said system;
(C) monitoring the stability of said target RNA sequence in said system; and
(D) identifying, characterizing or isolating said endogenous molecule able to modulate said deadenylation or degradation as capable of participating in the deadenylation or degradation of RNA or regulation thereof.

The molecule suspected of participating in the deadenylation or degradation of RNA or regulation thereof may be protein or RNA.

In another embodiment of the present invention, a method is provided for identifying an agent capable of modulating the degradation a target RNA sequence in the absence of deadenylation comprising (A) providing a cell extract in the presence of a nucleotide triphosphate;

(B) introducing said agent into said cell extract; and (C) monitoring the degradation of said target RNA sequence in said extract.

The present invention is also directed to kits for monitoring the stability of a preselected target RNA sequence under conditions capable of recapitulating regulated RNA turnover. Such kits comprise:

(a) cell extract optionally depleted of activity of proteins that bind polyadenylate;

(b) other reagents; and (c) directions for use of said kit.

A kit may further comprising nucleotide triphosphates, a reaction enhancer, a target RNA sequence, RNA binding proteins, RNA stability modifiers, or any combination thereof. It will be seen by the skilled artisan that the kits of the invention provide the components for carrying out the various methods disclosed herein, such as identifying agents and endogenous factors that modulate RNA turnover, identifying agents which modulate the RNA turnover activity of various factors involved in RNA turnover, and others, in particular use in the screening of small molecules for identifying potentially useful therapeutic agents for the prophylaxis and/or treatment of various conditions or diseases benefitted by modulating RNA turnover. The kits may be prepared to investigate either RNA deadenylation, RNA degradation, or both, depending on the components as described above. Furthermore, the cell extract may be partially purified. The kit may include reagents for depleting activity of proteins present in the extract which bind polyadenylate; such reagents, such as polyadenylate, polyadenylate bound to a matrix, an antibody to proteins that bind polyadenylate, and such an antibody bound to a matrix.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

ELAV Proteins Stabilize Deadenylated Intermediates in a Novel In Vitro mRNA Deadenylation/Degradation System Set forth herein is a novel in vitro mRNA stability system using Hela cell cytoplasmic S100 extracts and exogenous polyadenylated RNA substrates that reproduces regulated aspects of mRNA decay (turnover). The addition of cold poly(A) competitor RNA activated both a sequence-specific deadenylase activity in the extracts as well as a potent, ATP-dependent ribonucleolytic activity. The rates of both deadenylation and degradation were up-regulated by the presence of a variety of AU-rich elements in the body of substrate RNAs. Competition analyses demonstrated that trans-acting factors were required for RNA de-stabilization by AU-rich elements. The ~30 kDa ELAV protein, HuR, specifically bound to RNAs containing an AU-rich element derived from the TNF-α mRNA in the in vitro system. Interaction of HuR with AU-rich elements, however, was not associated with RNA destabilization. Interestingly, recombinant ELAV proteins specifically stabilized deadenylated intermediates generated from the turnover of AU-rich element-containing substrate RNAs. Thus, mammalian ELAV proteins play a role in regulating mRNA stability by influencing the access of degradative enzymes to RNA substrates.

The relative stability of mRNA is an important regulator of gene expression. The half-life of a specific mRNA can play a role in determining both its steady state level of expression, as well as the rate at which its gene product is induced (reviewed in Ross, 1995; Caponigro and Parker, 1996). Furthermore, mutations that affect the stability of mRNAs encoding regulatory factors can promote oncogenic transformation and immune dysregulation (Aghib et al., 1990; Schiavi et al., 1992). In general, many short-lived proteins, including those derived from cytokines and proto-oncogenes, are encoded by short-lived mRNAs. Several mRNAs that encode stable proteins, such as a-globin, have also been shown to have extraordinarily long half-lives (Holcik and Liebhaber, 1997). In addition, surveillance mechanisms that identify and reduce the half-lives of aberrant mRNAs that contain nonsense codon mutations have been described (Maquat, 1995; Jacobson and Peltz, 1996). Therefore, regulation of the half-life of mRNAs can have dramatic consequences on cellular responses and functional outcomes during growth and development.

Through the application of genetics, the mechanisms and factors involved in the turnover of mRNA in *Saccharomyces cerevisiae* are beginning to be identified. Multiple pathways of mRNA turnover are present in yeast, allowing for numerous levels of regulation and fine-tuning of gene expression. One general pathway of mRNA decay involves poly(A) tail shortening followed by decapping and 5'-to-3' exonucleolytic decay (Muhlrad et al., 1994). A second general pathway involves deadenylation followed by 3'-to-5' turnover of the body of the mRNA (Anderson and Parker, 1998). Endonucleolytic cleavage of some mRNAs has also been demonstrated (Presutti et al., 1995). Finally, another alternative decay pathway that bypasses deadenylation is involved in the translation-dependent degradation of nonsense codon-containing mRNAs (Weng et al., 1997). Several degradation enzymes and regulatory proteins that play a role in mRNA stability in yeast have been identified (Caponigro and Parker, 1996; Weng et al., 1997). Functionally significant interactions between the cap structure and the 3' poly(A) tail of yeast mRNAs have also been described (Tarun and Sachs, 1997). Whether these observations are generally applicable to mammalian cells, however, remains to be established.

In vivo observations are beginning to allow some generalizations concerning major pathways of mRNA turnover in mammalian cells. A poly(A) tail of approximately 200 bases is added to most mRNAs during processing in the nucleus (Colgan and Manley, 1997). The poly(A) tail serves at least two known functions in niRNA stability. First, in association with poly(A) binding proteins (Bernstein et al., 1989; Ford et al., 1997), it protects the mRNA from 3'-to-5' exonucleases. Second, the poly(A) tail serves as an initiation site for the turnover of the mRNA. The poly(A) tail can be progressively shortened throughout the lifetime of a mRNA in the cytoplasm. Controlling the rate of deadenylation appears to be an important regulatory point in mRNA stability (Wilson and Treisman, 1988; Xu et al., 1997). Once the poly(A) tail is shortened to approximately 30–65 bases, the body of the mRNA appears to be degraded in a rapid fashion in vivo without the accumulation of discernible intermediates (Chen et al., 1995; Xu et al., 1997). Little is known, however, concerning the enzymes and regulatory components involved in mammalian mRNA turnover.

In addition to the poly(A) tail, several cis-acting elements have been shown to play a role in mRNA stability. The 5' terminal cap structure protects the transcript from exonucleases (Furuichi et al., 1977). Several destabilizing elements (Caput et al., 1986; Shyu et al., 1989; Bonnieu et al., 1990; Peng et al., 1996), as well as stabilizing elements (Stefonovic et al., 1997), located in the body of the mRNA have also been identified. One well-characterized element that regulates inRNA stability is an AU-rich sequence (ARE) found in the 3' untranslated region of many short-lived mRNAs (Shaw and Kainen, 1986). These AREs primarily consist of AUUUA repeats or a related nonameric sequence (Lagnado et al., 1994; Zubiaga et al., 1995; Xu et al., 1997) and have been divided into three classes based on sequence characteristics and degradation kinetics (Xu et al., 1997). In general, AREs have been shown to increase the rate of deadenylation and RNA turnover in a translation-independent fashion (Chen et al., 1995; Fan et al., 1997). The underlying mechanism behind ARE function, however, remains to be determined.

Numerous proteins have been described that can bind iii vitro to AU-rich elements (e.g. Malter, 1989; Vakalopoulou et al., 1991; Bohjanen et al., 1991; Brewer, 1991; Levine et al., 1993; Hamilton et al., 1993; Katz et al., 1994; Nakagawa et al., 1995; Ma et al., 1996), but the exact role of each factor in the process of mRNA turnover remains to be defined. The ELAV family of ARE-binding proteins is evolutionarily conserved and differentially expressed in tissues throughout the development of vertebrates (reviewed in Antic and Keene, 1997). Although ELAV proteins have been found in both the cytoplasm and the nucleus (Gao and Keene, 1996), the most ubiquitously expressed form, HuR, can shuttle between the nucleus and the cytoplasm (Fan and Steitz, 1998; Peng et al., 1998; Atasoy et al, 1998). ELAV proteins play an important role in growth and development, as the Drosophila homolog is genetically essential for development and maintenance of the nervous system (Campos et al., 1985; Robinow and White, 1988). In addition, mammalian ELAV proteins are induced during differentiation and are distributed in RNP granules along dendrites (Gao and Keene, 1996). Several lines of evidence suggest that ELAV proteins control aspects of post-transcriptional gene expression (Gao and Keene, 1996; Koushika et al., 1996; Myer et al., 1997; Ma et al., 1997; Antic and Keene, 1998). Over-expression of ELAV family members, for example, has been shown to affect accumulation of selected mRNAs (Jain et al., 1997; Levy et al., 1998; Fan and Steitz, 1998; Peng et al., 1998). The precise role of ELAV proteins and other ARE-binding factors, however. remains to be established.

Mechanistic questions in mammalian cells are usually best approached using biochemical systems due to the inherent difficulties with mammalian cells as a genetic system. It has been difficult, however, to establish a versatile in vitro system to study mRNA stability and turnover. Based on in vivo observations and practical considerations, an optimal in vitro system to study the process of mRNA stability should have the following properties: First, the system should be efficient and highly reproducible. Second, minimal amounts (preferably undetectable) of RNA degradation in the system should be due to random degradation by non-specific contaminating ribonucleases. Third, deadenylation should occur before general degradation of the mRNA body is observed. Fourth, degradation of the mRNA body should occur in an apparently highly processive fashion without detectable intermediates. Fifth, regulation of the rate of overall deadenylation and degradation should be observed in a sequence-specific manner. Finally, the system should work on exogenous RNAs to allow ease of experimental manipulation.

Reported herein is the discovery of a new and useful in vitro mRNA stability system using cytoplasmic S100 extracts that fulfills all of the criteria listed above and possesses all of the properties known to be involved in ARE-mediated mRNA turnover. This system has been successfully used to demonstrate a role for the AU-rich element binding proteins of the ELAV family in mRNA stability. These findings indicate that ELAV proteins can affect a default pathway of ARE-mediated degradation by either protecting the mRNA from nuclease attack or by displacing factors that otherwise mark these short-lived transcripts for degradation. This in vitro system allows the identification of cellular factors involved in mRNA turnover and help elucidate mechanisms involved in the post-transcriptional regulation of gene expression.

Moreover, the in vitro system of the invention has ready applications in high throughput assays to screen libraries of compounds to elucidate which compounds may have applications as pharmaceuticals which can modulate the stability and turnover of RNA transcripts in vivo, and thus be used to treat a wide variety of disease or disorders.

i. Development of an In vitro System that Deadenylates and Degrades RNA Substrates The development of an in vitro system to study mRNA turnover requires the generation of a convenient source of poly(A)$^+$ RNA substrate and an active cellular extract. In order to obtain substrate RNAs that were both polyadenylated and easy to identify using standard acrylamide gel technology, a novel and versatile ligation-PCR approach that can attach a template encoding a 60 base poly(A) tail to the 3' end of DNA fragments that contain a Hind III site was used, and is described infra. In initial studies to develop an in vitro RNA stability system, a 60 base poly(A) tail was attached to a 54 base polylinker-derived sequence (Gem-A60). The small size of this polyadenylated transcript made it easy to analyze intermediates in the pathway of RNA turnover on acrylamide gels. Cellular extracts were prepared following a standard cytoplasmic S100 protocol (Dignam et al., 1983) using hypotonically lysed Hela spinner cells with minor variations as described in the Materials and Methods.

Gem-A60 RNA was incubated in S100 extracts in the presence of ATP. As seen in FIG. 1A (left panel), very little turnover of the Gem-A60 RNA was noted after 60 minutes of incubation. This reproducible slow rate of turnover prompted us to hypothesize that an inhibitor of the deadenylation/degradation process might be present in S100 extracts. This hypothesis was based on several observations. First, previous work with nuclear extracts determined that poly(A) binding proteins were strong inhibitors of a 3'-to-5' exonuclease activity (Ford et al., 1997). Second, the activity of a partially purified mammalian deadenylase preparation was inhibited by high amounts of PABP (Korner and Wahle, 1997). Third, over-expression of PABP in Xenopus oocytes inhibits maturation-specific deadenylation (Wormington et al., 1996). In order to test whether excess amounts of poly(A) binding proteins were responsible for inhibiting the deadenylation of Gem-A60 RNA in S100 extracts, increasing amounts of cold poly(A) competitor RNA were added to the reaction mixtures to sequester poly(A) binding proteins. As shown in FIG. 1A (right side), the addition of poly(A) competitor activated a degradation activity in the S100 extracts. The Gem-A60 RNA was shortened to a species slightly larger than the size of a deadenylated marker (Gem-A0) and approximately 30% of the input RNA was degraded. Titration experiments performed in coordination with UV cross-linking studies demonstrated that the amount of poly(A) competitor RNA required to activate the SlOO extract precisely corresponded with the ability of the competitor to inhibit binding of proteins to the poly(A) tail of the substrate RNA (data not shown). Furthermore, the nucleolytic activities activated by the addition of cold poly(A) RNA as competitor to the S100 extracts were still observable at concentrations of poly(A)>500 ng. These data suggest that the activated nuclease(s) is highly refractory to competition by poly(A).

Figure 1B:
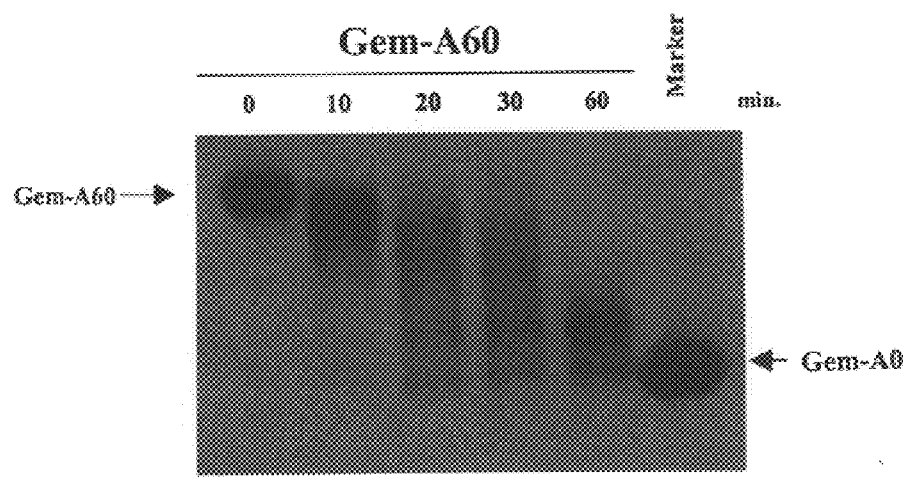
Figure 1C:
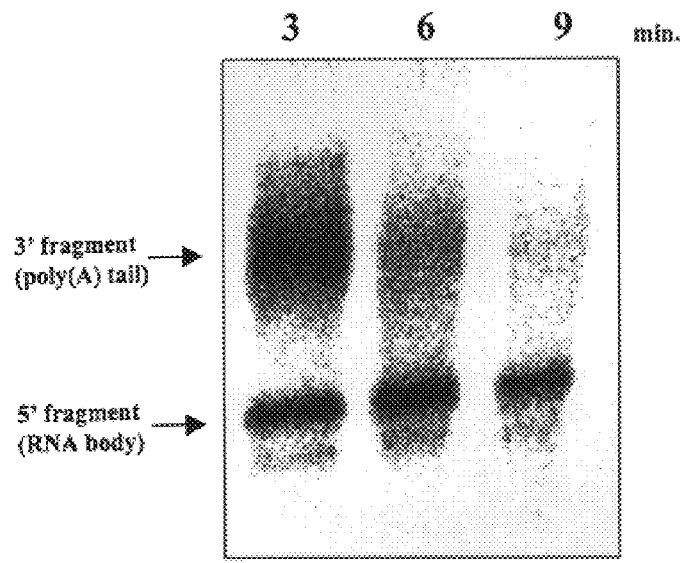
Figure 1D:

The progressive shortening of the Gem-A60 RNA substrate observed upon incubation in S100 extract supplemented with poly(A) competitor RNA was determined to be due to a 3'-to-5', poly(A) tail-specific exonuclease based on the following observations: First, RNA substrates $^{32}$P-labeled exclusively at their 5' cap structures were progressively shortened in the system in a similar fashion as uniformly labeled transcripts (compare FIGS. 1A and 1B). These data suggest that the shortening of the input RNA occurred in a 3'-to-5' direction. This conclusion was confirmed by separately analyzing the 5' and 3' portions of RNA products from the in vitro system by RNAse H digestion prior to gel electrophoresis. As shown in FIG. 1C, the 3' portion of the substrate RNA (which consists primarily of the 60 base poly(A) tail) was clearly being degraded before any turnover of the 5' portion of the transcript was detected. After 9 minutes of incubation, 72% of the 3' fragment containing the poly(A) tail is degraded, while only 19% of the 5' fragment has been turned over. Finally, in order to ascertain whether this 3'-to-5' exontIclease activity was indeed a poly(A)-specific deadenylase, we added 15 bases of non-adenylate sequence onto the 3' end of the Gem-A60 RNA (Gem-A60-15). As seen in FIG. 1D, while the Gem-A60 transcript (which contains a 3' poly(A) tail) is an excellent substrate for the 3' exonuclease activity, the Gem-A60-15 RNA, which has its poly(A) tract internalized 15 bases, was not.

From these data it has been concluded that the addition of poly(A) competitor RNA to an S100 extract activates a deadenylase which is active on exogenous, poly(A)+ substrate RNAs. The in vitro system reproduces several aspects of mRNA stability observed in vivo. The surprising observation that the deadenylase itself is not apparently inhibited by cold poly(A) suggests that the native enzyme may not have high affinity for its substrate. The deadenylase activity may contain additional RNA binding activities that anchor it to mRNAs, perhaps as part of a multi-component complex.

ii. RNA Turnover in the in Vitro System is Regulated by AU-rich Instability Elements.

Figure 2A:
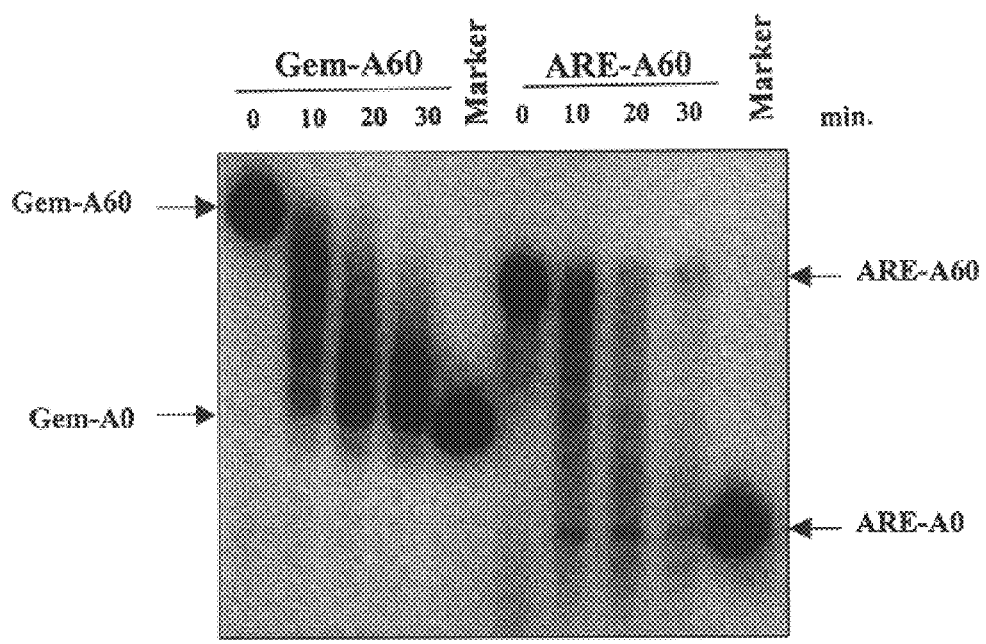
FIGS. 2A–E: The rate of transcript degradation in the in vitro system is regulated by AU-rich instability elements in a sequence-specific fashion.
Figure 2B:
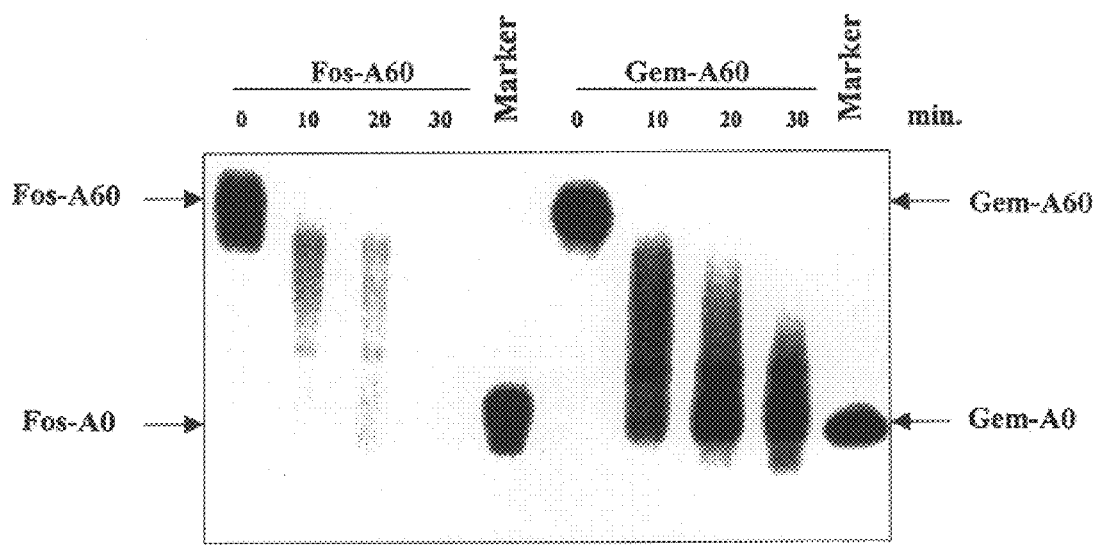
Figure 2C:
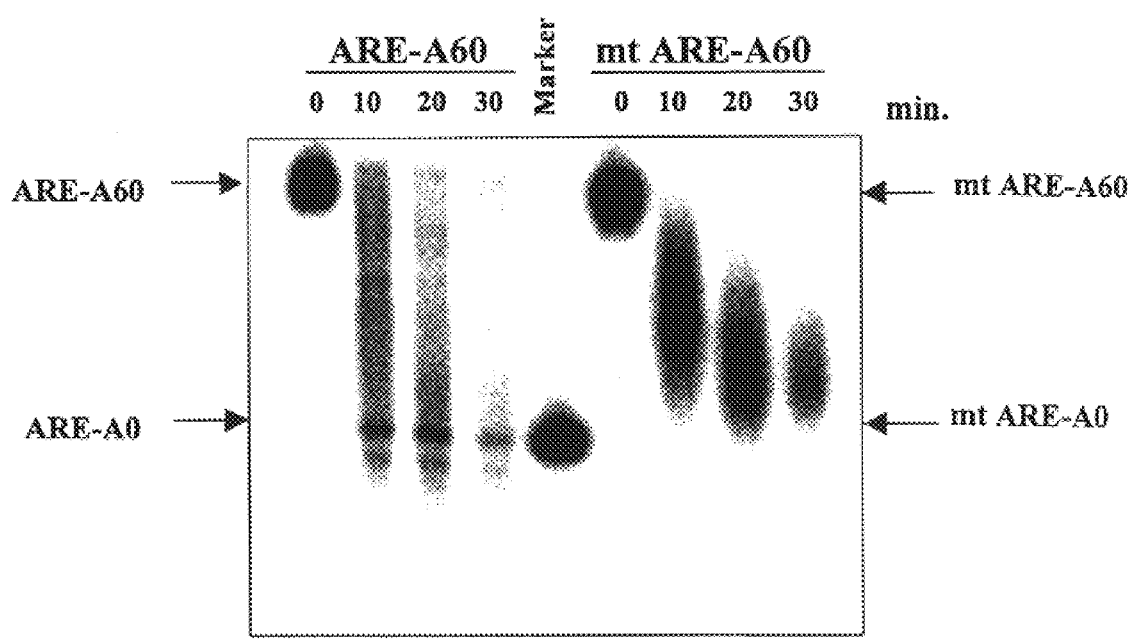

It was determined whether the RNA turnover activities exhibited by the S100 extract system could be influenced or modulated by sequences in the body of the transcript in a specific manner. The relative stability of small polyadenylated RNAs containing either a 54 base polylinker sequence (Gem-A60), a 34 base AU-rich element (ARE) from TNF-α mRNA (ARE-A60), or a 72 base ARE from the c-fos mRNA (Fos-A60) was determined in the in vitro stability system. As shown in FIGS. 2A and 2B, the turnover of both of the ARE-containing RNAs was dramatically increased compared to the Gem-A60 control transcript. To directly assess whether regulation by AREs was occurring in a sequence-specific fashion, the TNF-α-ARE was extensively mutated as described in Materials and Methods. Similar mutations in AU-rich instability elements were shown previously to greatly.iicrease mRNA half-life in vivo (Myer et al., 1997). As seen in FIG. 2C, mutations in the ARE reduced the rate and extent of deadenylation /degradation over 3-fold in the in vitro system. Thus, RNA turnover in the in vitro system can be regulated or modulated by AU-rich instability elements in a sequence-specific fashion.

Figure 2D:
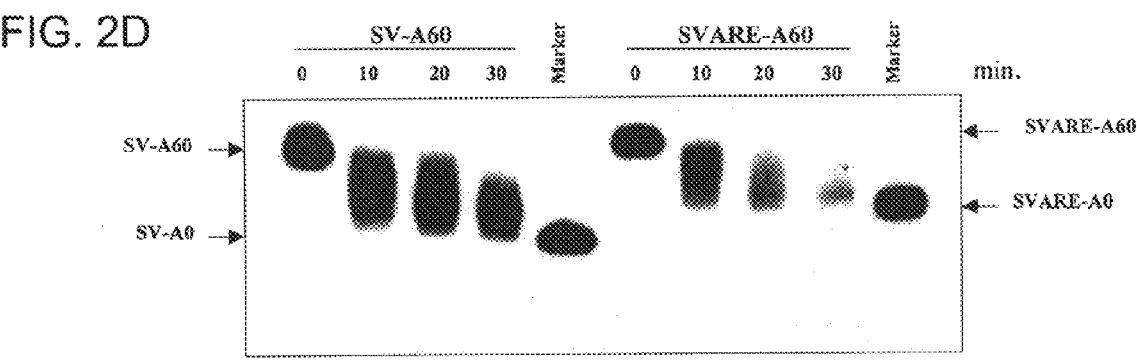
Figure 2E:
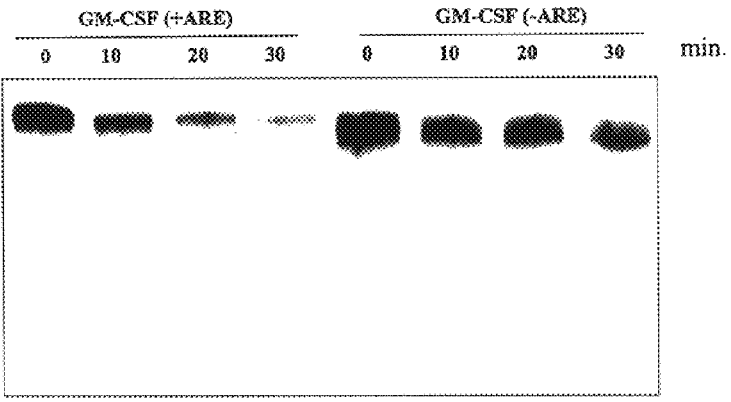

All of the RNA substrates we have examined above contain a body of approximately 50–70 bases attached to a poly(A) tail. It was then determined whether regulated turnover using larger polyadenylated RNA substrates could be detected in the system of the invention. As shown in FIG. 2D, a polyadenylated 250 base RNA derived from the 3' UTR of the SV40 late mRNA (SV-A60) was deadenylated but inefficiently degraded in the in vitro system. Adding the TNF-α-ARE to the 3' portion of this RNA (SVARE-A60) resulted in an approximate 3.5 fold increase in the rate of turnover. Finally, a nearly full length (~950 base) version of the human GM-CSF MRNA was prepared, as well as one in which the ARE was deleted (GM-CSF(–ARE)). The 3' ends of these transcripts were polyadenylated using yeast poly(A) polymerase (Martin and Keller, 1998). Gel purified RNAs were incubated in the in vitro stability system and aliquots were removed at the times indicated. As seen in FIG. 2E, the version of the GM-CSF mRNA that contains an ARE was approximately 2.5 fold less stable than GM-CSF(–ARE) in the in vitro system. As seen above with other transcripts, the GM-CSF transcripts were also deadenylated in the system. Deadenylation was not observable in FIG. 2E due to the lack of resolution of the gel system employed, but can be observed using formaldehyde-agarose gels (data not shown).

iii. Degradation But Not Deadenylation, Requires ATP

Figure 3A:
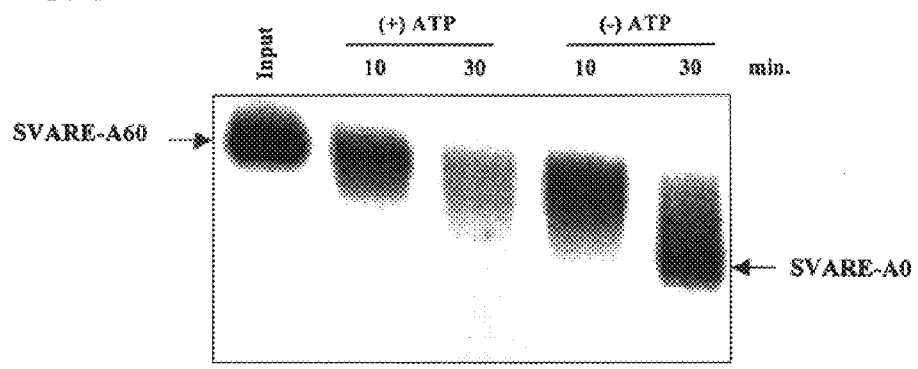
FIGS. 3A–B: Deadenylation occurs in the absence of ATP and is regulated by AU-rich elements in vitro.
Figure 3B:
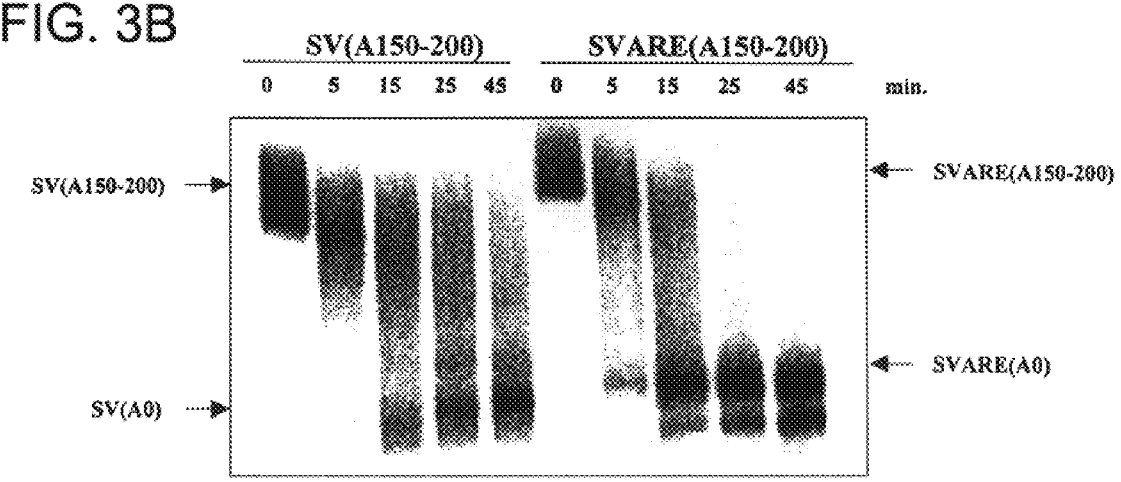

Transcripts with 60 adenylates at the 3' end were observed to undergo both deadenylation and turnover in the in vitro system. This is consistent with in vivo observations that suggest the poly(A) tail is shortened to about 30–65 bases before mRNA turnover is observed (Xu et al., 1997). Since degradation appeared to begin before the input transcript was completely deadenylated (eg. FIG. 2), it was difficult to quantitatively assess the effects of AU-rich elements on relative deadenylation rates. In order to try uncoupling these processes and accurately evaluate the effect of AREs on deadenylation rates in the in vitro system, we surveyed the cofactor requirements that might be unique to either deadenylation or turnover. Both processes were inhibited by the addition of EDTA (data not shown), suggesting a role for divalent cations. Curiously, deadenylation could occur without the addition of ATP/phosphocreatine to the system (FIG. 3A). Degradation, on the other hand, required ATP/ phosphocreatine as indicated by the accumulation of deadenylated intermediates in its absence (FIG. 3A, lanes— ATP). By omitting ATP from the reaction, therefore, we were able to evaluate relative deadenylation rates in the presence or absence of an AU-rich instability element. RNAs with physiological length poly(A) tails (150–200 bases) which lack (SV-A 150–200) or contain (SVARE-A 150—200) an ARE were incubated in the in vitro system and aliquots were analyzed at the times indicated. As seen in FIG. 3B, RNA substrates containing an ARE were deadenylated at an approximately two fold faster rate than RNAs that do not contain the instability element.

In summary, an in vitro i-nRNA stability system has been discovered that acts on exogenous substrates and faithfully reproduces all of the known in vivo aspects of turnover. RNAs are first deadenylated prior to degradation of the body of the transcript. Degradation of the body of the mRNA then occurs in an apparently highly processive fashion with no discernible intermediates. Deadenylation and decay rates are increased several fold by the inclusion of an AU-rich instability element. ARE regulation of RNA stability is sequence-specific and highly reproducible, as all three of the AREs we have tested in the in vitro system function in a similar fashion. This system should provide a valuable means to elucidate mechanistic aspects of regulated and general mRNA turnover pathways.

iv. The Role of ARE Binding Proteins in the in vitro System.

The in vitro system described here allows evaluation of the role of ARE-binding proteins in the process of RNA deadenylation/degradation. Several proteins were found to be associated with ARE-containing RNAs in our extracts. As seen in FIG. 4A, a protein of ~30 kDa and a group of ~40 kDa proteins were specifically UV cross-linked to the short ARE-A60 transcript. A species of approximately 70 kDa was also detected when this ARE was inserted into a larger transcript (SVARE-A60; see FIG. 5B). It is possible that this 70 kDa protein was not detected on the ARE-A60 RNA because of the relatively small size of the transcript. Efforts to determine the identity of these cross linked species using available antibodies to known ARE-binding proteins revealed the presence of an ELAV protein. As shown in FIG. 4B, immunoprecipitation assays identified the 30 kDa protein as HuR (a.k.a. HuA), a member of the ELAV protein family that is ubiquitously expressed in all tissues (Good, 1995; Ma et al., 1996; Myer et al., 1997). Antisera against another RNA-binding protein of approximately 30 kDa, hnRNP A1, failed to detect any cross linked protein in our system (FIG. 4B). Two additional antisera were tested in order to identify the 40 kDa band. Antibodies to hnRNP C protein failed to detect any cross linked protein, while antisera to AUF-1 (a.k.a. hnRNP D)(Brewer, 1991) did precipitate a small amount of cross linked 40 kDa protein (data not shown). However, this cross linked product was not competed by increasing amounts of a 34 base synthetic ARE competitor RNA (data not shown). The significance of this low level of non-specific AUF-1 cross linking in the system is unclear. It was concluded that the 30 kDa species that specifically cross links to the ARE element is HuR, a protein that has been previously suggested to play a role in ARE-mediated mRNA decay (Vakaloloupou et al, 1991; Antic and Keene, 1997; Myer et al., 1997).

Figure 5A:
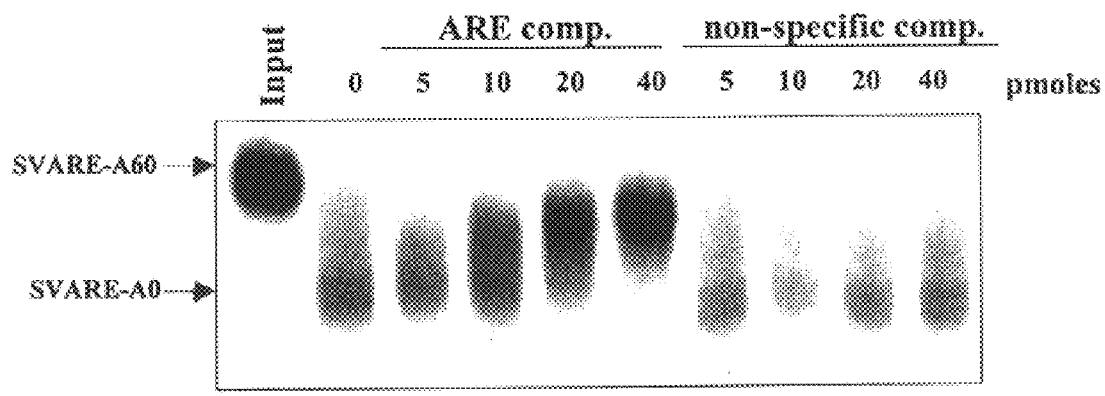
FIGS. 5A–C: While AU-rich element binding factors are important to promote RNA deadenylation and degradation, the binding of the HuR protein to AU-rich elements is not associated with AU-rich element-mediated transcript instability.

Next, it was determined whether the interaction of the cross linked ARE binding proteins with the element was required to mediate instability. Synthetic ribonucleotides containing either a 34 base TNF-α ARE or randomly chosen, non-ARE sequences were used. Synthetic competitor RNAs were added in increasing amounts to the in vitro stability system and their effect on RNA turnover was assessed. As seen in FIG. 5A, the ARE competitor RNA completely inhibited deadenylation and degradation at 40 pm, while the non-specific RNA had no effect at similar concentrations. The ARE competitor RNA had a similar effect on the deadenylation/degradation of RNAs whether or not they contained an ARE. Thus, factors capable of interacting with AREs are important for deadenylation, and may be a part of a multi-protein deadenylase/degradation complex.

Figure 5B:
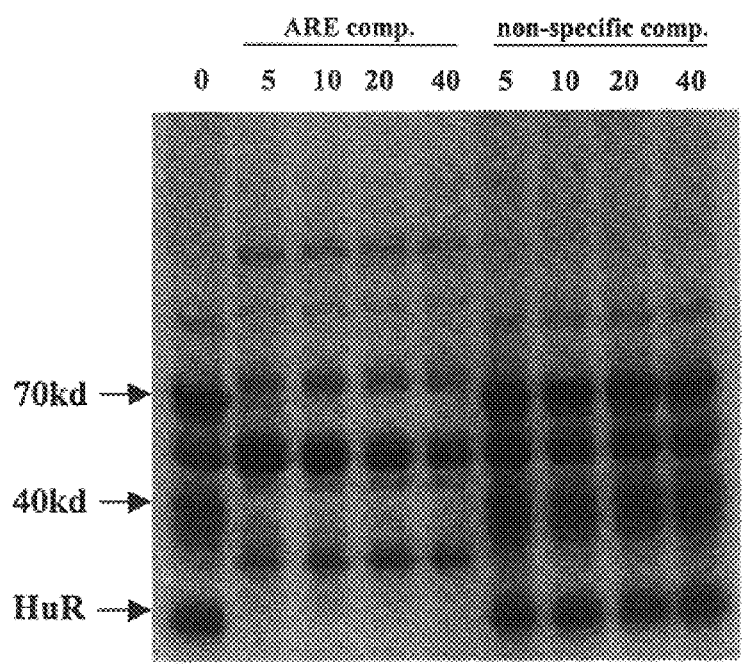
Figure 6A:
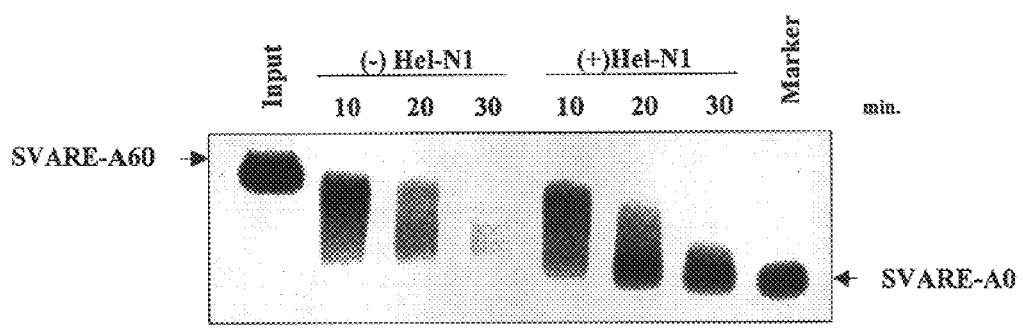
FIGS. 6A–D: ELAV proteins specifically stabilize deadenylated intermediates in the in vitro system.
Figure 6B:
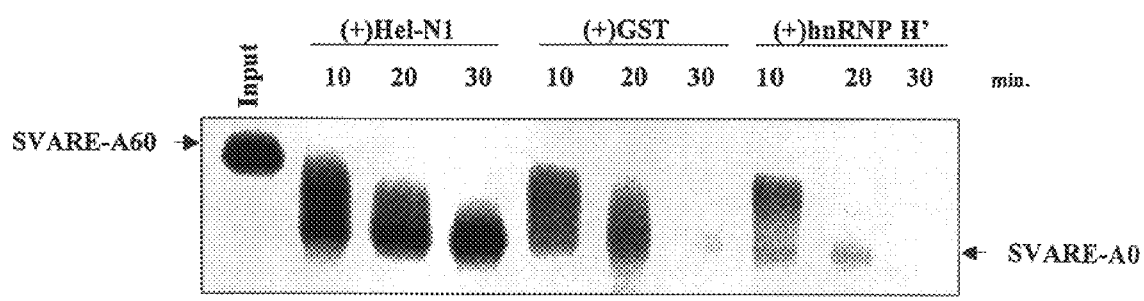

The ability of the synthetic ARE competitor RNA to block deadenylation was compared with the ability of the RNA to compete for interaction of ARE-binding proteins with the substrate transcript. EDTA was added to cross-linkinig assays to inhibit RNA turnover and to evaluate the effect of various levels of competitor on cross-linking/label transfer efficiency. As shown in FIG. 5B, all ARE-binding proteins (including HuR protein that could be immunoprecipitated using specific antisera prior to gel electrophoresis as shown in panel C) were specifically competed from the SV-ARE-A60 RNA substrates upon addition of 5 pm of the synthetic RNA competitor. As shown in FIG. 5A, however, 5 pm of synthetic ARE competitor RNA failed to have an appreciable effect on the rate of RNA deadenylation/degradation in the system. Hence, none of the ARE-binding proteins that could be detected by cross-linking appear to be required for deadenylation/degradation in the in vitro system.

v. ELAV Proteins Prevent Degradation of Deadenylated Transcripts in the in Vitro System Since the ARE binding proteins we detected by cross-linking do not appear to be required for deadenylation/degradation, they may play a role in transcript stability. Consistent with this model, recent in vivo data suggest that overexpression of Hel-N1 and HuR proteins can stabilize ARE-containing transcripts (Jain et al., 1997; Fan and Steitz, 1998; Peng et al., 1998). A mouse recombinant HuR protein, as well as other members of the ELAV family (Hel-N1 and Hel-N2 [a.k.a. HuB]) were produced as GST fusion proteins and added these to the in vitro stability system at a 10:1 molar ratio to substrate RNA. Similar data were obtained using any of the three recombinant ELAV family proteins, and only data with rHel-N1 is shown. As seen in FIG. 6A, rHel-N1 protein failed to affect deadenylation of the SVARE-A60 RNA substrate in the in vitro system, but stabilized a deadenylated intermediate. GST alone, or another GST-fusion protein that binds RNA (hnRNP H') had no effect on transcript stability in the in vitro system (FIG. 6B). As a result, it was concluded that the ELAV family of RNA binding proteins function to protect deadenylated transcripts from the degradation enzymes.

Figure 6C:
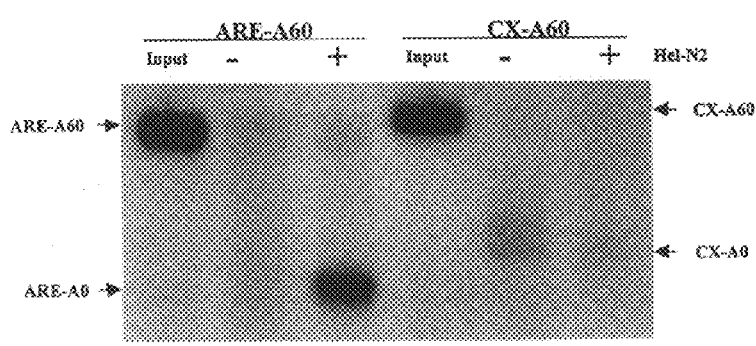
Figure 6D:
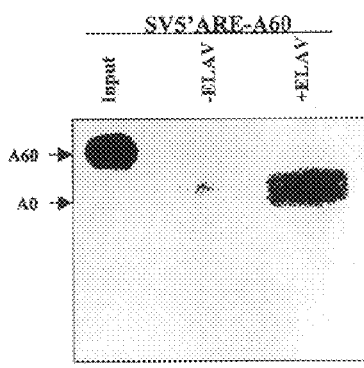

Next, it was tested whether the RNA substrate must contain an ARE in order for rELAV proteins to stabilize a deadenylated intermediate in the in vitro system. ARE-A60 RNA, or an unrelated but similarly sized and polyadenylated transcript, CX-A60, were incubated in the in vitro system in the presence or absence of rELAV proteins. As seen in FIG. 6C, rHelN1 (or other rELAV proteins [data not shown]) stabilized the deadenylated intermediate only from RNAs that contain an ARE binding site. Thus, the stabilization of deadenylated intermediates by ELAV proteins requires an ARE. Furthermore, ELAV proteins can stabilize a deadenylated intermediate whether the ARE is located at the 3', 5' or central positions of the 250 base SVARE-A60 RNA. These data indicate that the ARE-ELAV protein complex probably is not simply preventing turnover through steric blocking of an end of the transcript, thereby preventing exonuclease access.

Set forth herein is a novel and useful in vitro RNA stability system that faithfully reproduces many known aspects of in vivo mRNA turnover in mammalian cells. Exogenous RNA substrates are deadenylated before degradation of the RNA body occurs in an apparently highly processive fashion without detectable intermediates. Furthermore, the rates of RNA deadenylation and degradation are regulated by AU-rich elements in the system in a sequence-specific manner. The system of the invention has been successfully used to determine a role for the ELAV family of ARE binding proteins in the stability of deadenylated transcripts by specifically blocking the degradation step. These data illustrate the value of the system to address the mechanism of regulated mRNA turnover.

The in vitro system described in this report has several key technical advantages that significantly increase its utility. First, the system is highly reproducible and uses standard S100 cytoplasmic extracts from Hela spinner cells. In fact, nine independent preparations of S100 extract that all fuinction in the assay in a similar fashion have been tested. The only difference among extracts appears to be in the kinetics of turnover (e.g. compare the slight differences in the pattern of turnover of Gem-A60 RNA in FIG. 1A with the pattern observed in FIG. 1D). Second, the extracts exhibit minimal background degradation of RNA due to non-specific nucleases. This lack of noise in the system significantly contributes to its reproducibility. Another key element of the system is that is uses exogenous polyadenylated RNAs as substrates. This property affords variety in RNA substrate preparation and sequence manipulation. Fourth, the system exhibits sequence-specific regulation by AU-rich elements in the absence of translation. In total, these technical advantages make the system a valuable reagent to identify components involved in mRNA turnover and address the mechanism of regulated mRNA stability.

The addition of poly(A) competitor RNA was required to activate S100 extracts to efficiently deadenylate and degrade RNAs in a regulated manner. Titration of cold poly(A) demonstrated that the extracts became activated for deadenylation/degradation when sufficient competitor was added to substantially reduce cross linking of a 70 kDa poly(A) binding protein to the poly(A) tail of the radiolabeled substrate RNA (data not shown). Surprisingly, the deadenylation in the extracts remain active even in the presence of>500 ng of poly(A). Commercial poly(A) preparations prepared with polynucleotide phosphorylase, therefore, do not appear to be able to interact with and sequester the deadenylase enzyme. These data suggest that the deadenylase activity is either in extraordinary concentrations in the extracts or may not have a strong affinity for its substrate. In conjunction with this, it has been observed that an increase in deadenylation rate of ARE containing RNAs (FIGS. 2 and 3), as well as the ability of the ARE competitor RNA to inhibit deadenylation of non-ARE containing substrates. These data suggest that ARE-binding proteins may be associated with the deadenylase activity.

Moreover, HuR protein, a ubiquitously expressed member of the ELAV family of RNA binding proteins (Good, 1995; Ma et al., 1996; Myer et al., 1997; Antic and Keene, 1997), has been identified as one of the major ARE binding factors in the system of the invention. Also, the system of the invention has been successfully used to detect weak binding to AUF-1 (hnRNP D), a protein previously speculated to be involved in regulated mRNA decay in vitro (DeMaria and Brewer, 1996). AUF-1, therefore, does not appear to play a significant role in transcript instability in our system. ELAV proteins are not required for deadenylation/degradation, but rather play a role in the stability of deadenylated RNAs that contain an ARE (FIG. 6). These data suggest that in addition to its effect on deadenylation rates (Chen et al., 1995; Xu et al., 1997), the ARE influences the efficiency of turnover of the body of the mRNA. In vivo observations (Chen et al., 1995; Xu et al., 1997; Peng et al., 1998) also support the conclusion that ARE influences mRNA degradation rates.

ELAV proteins, therefore, appear to regulate mRNA stability in vitro, an observation consistent with in vivo transfection studies. The ELAV family comprises four members, three of which are expressed in a tissue or developmental specific manner (reviewed in Antic and Keene, 1997). Tissue-specific ELAV proteins are also localized primarily to the cytoplasm, while the ubiquitous HuR protein is predominantly nuclear and can redistribute to the cytoplasm (Atasoy et al., 1998; Peng et al., 1998; Fan and Steitz, 1998). It has been suggested that differentially expressed ELAV proteins play a role in regulating the stability of both nuclear and cytoplasmic RNA, thereby fine tuning gene expression in specific developmental states (Gao and Keene, 1996; Antic and Keene, 1998).

Figure 5C:
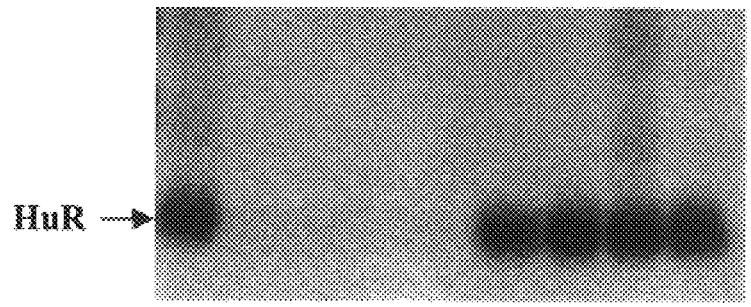

The competition data shown in FIG. 5 clearly demonstrate that factors associated with the ARE are required for deadenylation/degradation of substrate RNAs. Based on the kinetics of competition, these factors must either be much more abundant than the cross-linkable ARE binding proteins like HuR, or interact with the ARE with a much lower affinity. We favor the latter model, and suggest that these factors are part of a multi-component complex that includes the deadenylase and degradation enzymes. Through multiple cooperative interactions, these weak ARE binding components may allow efficient assembly of the deadenylase/degradation complex on ARE containing transcripts while still allowing the complex to assemble, albeit less effectively, on non-ARE containing RNAs. The RNA binding components of this proposed complex also may have affinity for other non-ARE instability elements (e.g. Peng et al., 1996).

The observation that endogenous HuR protein in S100 extracts set forth herein can be cross-linked to ARE-containing RNA substrates (FIG. 5) makes it surprising that an ARE can function as a destablizing element in the in vitro assay. Since HuR protein is predominantly nuclear, however, only low levels of the protein are likely to be present in our cytoplasmic extracts. This low level of HuR protein is probably unable to efficiently compete with destablizing factors for binding to the ARE. In fact, sequestration of the HuR protein by the addition of low levels of synthetic ARE coinmpetitor RNA does lead to an increased rate of turnover of ARE-containing RNAs in the in vitro system. As shown in FIG. 5A, the amount of SVARE-A60 RNA remaining after 30 min. in the system in the absence of competitor RNA (lane 0) is approximately 20% greater than when the assay is done in the presence of 5 pm of ARE competitor RNA (lane 5 pm). The removal or sequestration of HuR protein in S100 extracts, therefore, may be necessary in order to observe regulated deadenylation and degradation in some instances.

Materials and Methods

Transcription Templates and RNAs

RNAs were produced by in vitro transcription using SP6 polymerase (Melton et al., 1984) in the presence of $^{7in}$GpppG cap analog and radiolabeled UTP or ATP as indicated. All transcripts were gel purified prior to use. For RNAs labeled exclusively at the 5' cap, transcription reactions were performed in the absence of cap analog and radioactive nucleotides. Capping was then performed using guanyltransferase (BRL) and radiolabled GTP according to the manufacturer's recommendations. The sequence of short RNAs used as substrates in the in vitro system is shown in Table 1.

Transcription templates were derived as follows (Please note that all synthetic oligonucleotides used as transcription templates shown below contain a 24 base SP6 promoter fragment at their 5' ends): Gem-A0 RNA was produced from Hind III cut pGem4 (Promega). Gem-A60- 15 RNA was produced from the PCR product used to produce Gem-A60 RNA (see below) without removing the primer binding site with Ssp I . Templates for ARE-A0 RNA were generated by hybridizing the synthetic oligonucleotide 5'-ATTTAGGTGACACTATAGAATACACATTATTTA TTATTTATTTATTATTTATTTATTTA-3'(SEQ ID NO: 1) and its appropriate complement. Templates for MT-ARE-A0 RNA were generated by hybridizing the synthetic oligonucleotide 5'-ATTTAGGTGACACTATAGAATACACGTTAGIA TTCATTTGTTTACTATTGATTFCTTTA-3'(SEQ ID NO:2) and its appropriate complement. Templates for Fos-A0 RNA were generated by hybridizing the synthetic oligonucleotide 5'-ATTTAGGTGACACTATAGAATACACAAATTTT ATTGTGTTTTTAATTTTATTTATTAAGATGGATTCTC-3'(SEQ ID NO:3) and its appropriate complement. The template for SV-A0 RNA was Hind III cut pSVL-Gem (Wilusz et al., 1988). Templates for SVARE-A0 RNA were generated by inserting the TNF-α ARE containing oligonucleotide 5'-ATTATTTATTATTTATTTATTATTTATTATTTA (SEQ ID NO:4) and its appropriate complement between the PstI and Hind III sites of pSVL-Gem (located near the 3' end of the RNA). SVARE-A0 RNA was transcribed from Hind III linearized DNA. The template for GM-CSF (+ARE) RNA was EcoRI cut pGM-CSF (Shaw and Kamen, 1986). The template for GM-CSF (−ARE) RNA was NcoI cut pGM-CSF. Templates for CX-A0 RNA were generated by hybridizing the synthetic oligonucleotide 5'-ATTTAGGTGACACTATAGAATACACCCCAACGG GCCCTCCCTCCCCTCCTTGCACCAT-CATCGCATCACG (SEQ ID NO:5) and its appropriate complement.

Synthetic RNAs used in competition studies were made by the NJMS Molecular Core Facility and contained the following sequences: ARE: 5'AUUAUUUAUUAUUUAU-UUAUUAUUUAUUUAUUUA (SEQ ID NO:6); Non-specific competitor: 5'-GUCACGUGUCACC (SEQ ID NO:7).

Addition of Poly(A) Tails to Transcripts

A template for a 60 base poly(A) tail was added to DNA templates using a ligation/PCR protocol have recently been described (Ford et al., 1997). Briefly, all of the templates described above contain a Hind III site that is used to generate the 3' end of the RNA. The synthetic oligonucleotide 5'-AGCTA$_{60}$TATTGAGGTGCTCGAGGT (SEQ ID NO:8) and its appropriate complement were generated, hybridized, and ligated to Hind III cut DNA templates. Ligation products were amplified using an SP6 promoter primer (5'-CATACGATTTAGGTGACACTATAG (SEQ ID NO:9)) and a primer specific for the 3' end of the ligated oligonucleotide (5'-ACCTCGAGCACCTC (SEQ IDNO:10)). Amplified products were purified on Centricon 100 columns, cut with SspI, and used as templates for SP6 polymerase generate RNAs carrying the 'A60' designation. Poly(A) polymerase (Amersham) was used to add 150–200 base poly(A) tails onto transcripts. RNAs were incubated with enzyme according to the manufacturer's recommendations on ice for 5–8 min. Following the reaction, RNAs were extracted with phenol-chloroform, ethanol precipitated, and purified on 5% acrylamide gels containing 7M urea to obtain RNAs with the appropriate amount of poly(A) at the 3' end.

S100 Extract Production

Cytoplasmic extracts were prepared from Hela spinner cells grown in JMEM supplemented with 10% horse serum as described by Dignam et al (1983) with the following two modifications. First, following centrifugation at 100,000×g for 1 hr, the supernatant was adjusted to 10% glycerol prior to dialysis. Second, dialysis times were shortened to 30 min. Extracts were stored at −80° C.

In Vitro RNA Deadenylation/Degradation System

Typically, approximately 200,000 cpm (~50 fm) of gel purified RNA is used per reaction. In comparative studies, equal molar amounts of transcripts were used. A typical 14.25 μl reaction mixture contains 3.25 μl of 10% polyvinyl alcohol, 1 μl of a 12.5 mM ATP/250 mM phosphocreatine mixture, 1 μl of 500 ng/ul poly(A) (Pharmacia), 1 μl of RNA and 8 μl of dialyzed extract. Reactions were incubated at 30° C. for the times indicated and stopped by the addition of 400 μl of stop buffer (400 mM NaCl, 25 mM Tris-CI, pH 7.6, 0.1% SDS). Reaction mixtures were phenol extracted, ethanol precipitated and analyzed on a 5% acrylamide gel containing 7M urea. All quantitation was performed using a Molecular Dynamics Phosphorinager.

Recombinant ELAV proteins (HuR, Hel-N1 and Hel-N2) were made as GST-fusion proteins in *E. coli* and purified using glutathione-sepharose affinity chromatography according to the manufacturer's recommendations (Levine et al, 1993).

RNase H Digestion ARE-A60 RNA, radiolabeled at A residues, was incubated in the in vitro stability system for the times indicated. RNA products were phenol extracted and concentrated by ethanol precipitation. The sample was resuspended in a final volume of 30 μl containing 20 mM Tris-Cl, pH 8.0, 100 mM NaCl, 10 mM MgCl$_2$, 1 mM DTT, 100 picomoles of the antisense oligonucleotide 5'-AGTTAAATAAAT (SEQ ID NO:11), and 1 unit of RNase H. Reactions were incubated at 37° C. for 30 min. and products were analyzed on a 5% acrylamide gel containing 7 M urea.

UV Cross Linking and Immunoprecipitations

UV cross linking/label transfer experiments were performed as described previously using a Sylvania G15T8 germicidal light (Wilusz and Shenk, 1988). Cross linking experiments were done in the presence of 25 mM EDTA to inhibit RNA turnover to allow for accurate comparisons between samples. Following digestion with RNAses A, T1 and T2, cross linked proteins were analyzed on 10% acrylamide gels containing SDS.

For immunoprecipitation analysis following UV cross linking and RNAse treatment, 300 μl of RIPA buffer (0.1ISM NaCI, 1% NP-40, 0.5% deoxycliolate, 0.1% SDS and 50 mM Tris-CI, pH 7.6) was added to samples. Following a brief centrifugation in a microfuge, precleared samples were incubated on ice with antibodies for 1 hr. Antigen-antibody complexes were collected using formaliii fixed, washed protein-A positive S. aureus cells, washed five times using RIPA buffer, and analyzed on a 10% acrylamide gel containing SDS. Antibodies specific for GRSF (Qian and Wilusz, 1994) and hnRNP A1 (Wilusz and Shenk, 1990) have been described previously. The preparation and characterization of rabbit polyclonal antibodies specific for HuR will be described elsewhere (Atasoy et al., 1998).

Aghib, D. F., Bishop, J. M., Ottolenghi, S., Guerrasio, A., Serra, A., and Saglio, G. 1990. A 3' truncation of myc caused by chromosomal translocation in a human T-cell leukemia increases mRNA stability. Oncogene 5: 707–711.

Anderson, J. S. J., and Parker, R. 1998. The 3' to 5' degradation of yeast mRNAs is a general mechanism for mRNA turnover that requires the SK12 DEVH box protein and 3' to 5' exonuclease of the exosome complex. EMBO J. 17: 1497–1506.

Antic, D., and Keene, J. D. 1997. Embryonic lethal abnormal visual RNA-binding proteins involved in growth, differentiation, and posttranscriptional gene expression. Am. J. Hum. Genet. 61: 273–278.

Antic, D., and Keene, J. D. 1998. Messenger ribonucleoprotein complexes containing human ELAV proteins: interactions with cytoskeleton and translational apparatus. J. Cell. Sci. 111: 183–197.

Atasoy, U., Watson, J., Patel, D., and Keene, J. D. 1998. Ubiquitously-expressed ELAV RNA binding protein, HuA, is upregulated during serum stimulation and T cell activation and undergoes nuclear/cytoplasmic shuttling. J. Cell Sci., In Press.

Bernstein, P., Peltz, S. W., and Ross, J. 1989. The poly(A)-poly(A) binding protein complex is a major determinant of mRNA stability in vitro. Mol. Cell. Biol. 9: 659–670.

Bonnieu, A., Roux, P., Marty, L., Jeanteur, P., and Piechaczyk 1990. AUUUA motifs are dispensable for rapid degradation of the mouse c-myc mRNA. Oncogene 5: 1585–1588.

Bohjanen, P. R., Bronislawa, P., June, C. H., Thompson, C. B., and Lindsten, T. 1991. An inducible cytoplasmic factor (AU-B) binds selectively to AUUUA multimers in the 3' untranslated region of lymphokine mRNA. Mol. Cell. Biol. 11: 3288–3295.

Brewer, G. 1991. An A+U rich element RNA-binding factor regulates c-myc mRNA stability in vitro. Mol. Cell. Biol. 11: 2460–2466.

Brown, C. E., Tarun Jr., S. Z., Boeck, R., and Sachs, A. B. 1996. PAN3 encodes a subunit of the Pab 1 p-dependent poly(A) nuclease in *Saccharomyces cerevisiae*. Mol. Cell. Biol. 16: 5744–5753.

Campos, A. R., Grossman, D., and White, K. 1985. Mutant alleles at the locus elav in Drosophila melanogaster lead to nervous system defects: a developmental-genetic analysis. J. Neurogenet. 2:197–218.

Caponigro, G. and Parker, R. 1996. Mechanism and control of mRNA turnover in *Saccharomyces cerevisiae*. Microbiol. Rev. 60: 233–249.

Caput, D., Beutler, B., Hartog, K., Thayer, R., Brown-Shimer, S., and Cerami, A. 1986. Identification of a common nucleotide sequence in the 3'-untranslated regions of mRNA molecules specifying inflammatory mediators. Proc. Natl. Acad. Sci. USA 83: 1670–1674.

Chen, C.-Y.A, Xu, N., and Shyu, A.-B. 1995. MRNA decay mediated by two distinct AU-rich elements from c-fos and GM-CSF transcripts: different deadenylation kinetics and uncoupling from translation. Mol. Cell. Biol. 15: 5777–5788.

Colgan, D. F., and Manley, J. L. 1997. Mechanism and regulation of mRNA polyadenylation. Genes Dev. 11: 2755–2766.

DeMaria, C. T., and Brewer, G. 1996. AUF 1 binding affinity to A+U-rich elements correlates with rapid mRNA degradation. J. Biol. Chem. 271: 12179–12184.

Dignam, J. D., Lebovitz, R. M., and Roeder, R. G. 1983. Accurate transcription initiation by RNA polymerase 11 in a soluble extract from isolated mammalian nuclei. Nucl. Acids Res. 11: 1475–1489.

Fan, X. C., Myer, V. E., and Steitz, J. A. 1997. AU-rich elements target small nuclear RNAs as well as mRNAs for rapid degradation. Genes Dev. 11: 2557–2568.

Fan, X. C., and Steitz, J. A. 1998. Overexpression of HUR, a nuclear-cytoplasmic shuttling protein, increases the in vivo stability of ARE-containing mRNAs. EMBO J. 17: 3448–3460.

Ford, L. P., Bagga, P. S., and Wilusz, J. 1997. The poly(A) tail inhibits the assembly of a 3'-to-5' exonuclease in an in vitro RNA stability system. Mol. Cell. Biol. 17: 398–406.

Furuichi,Y., LaFiandra, A., and Shatkin, A. J. 1977. 5'-terminal structure and mRNA stability. Nature 266: 235–239.

Gao, F. B., and Keene, J. D. 1996. Hel-N1/Hel-N2 proteins are bound to poly(A)+mRNA in granular RNP structures and are implicated in neuronal differentiation. J. Cell Sci. 109: 579–589.

Good, P. J. 1995. A conserved family of elav-like genes in vertebrates. Proc. Natl. Acad. Sci. USA. 92: 4557–4561.

Hamilton, B. J., Nagy, E., Malter, J. S., Arrick, B. A., and Rigby, W.F.C. 1993. Association of heterogeneous nuclear ribonucleoprotein A1 and C proteins with reiterated AUUUA sequences. J. Biol. Chem. 268: 8881–8887.

Holcik, M., and Liebliaber, S. A. 1997. Four highly stable eukaryotic mRNAs assemble 3' untranslated region RNA-protein complexes sharing cis and trans components. Proc. Natl. Acad. Sci. USA 94: 2410–2414.

Jain, R. G., Andrews, L. G., McGowan, K. M., Pekala, P. H., and Keene, J. D. 1997. Ectopic expression of Hel-N 1, an RNA binding protein, increases glucose transporter (GLUT 1) expression in 3T3-L1 adipocytes. Mol. Cell. Biol. 17: 954–962.

Jacobson, A., and Peltz, S. W. 1996. Interrelationships between the pathways of mRNA decay and translation in eukaryotic cells. Annu. Rev. Biochem. 65: 693–740.

Katz, D. A., Theodorakis, N. G., Cleveland, D. W., Lindsten, T., and Thompson, C. B. 1994. AU-A, an RNA binding activity distinct from hnRNP A1, is selective for AUUUA repeats and shuttles between the nucleus and the cytoplasm. Nucl. Acids Res. 22: 238–246.

Korner, C. G., and Walile, E. 1997. Poly(A) tail shortening by a mammalian poly(A)-specific 3'-exoribonuclease. J. Biol. Chem. 272: 10448–10456.

Koushika, S. P., Lisbon, M. J., and White, K. 1996. ELAV, a Drosophila neuron-specific protein, mediates the generation of an alternatively spliced neural protein isoform. Curr. Biol. 6: 1634–1641.

Lagnado, C. A., Brown, C. Y., and Goodall, G. J. 1994. AUUUA is not sufficient to promote poly(A) shortening and degradation of a in RNA: the fuinctional sequence within AU-rich elements may be UUAUUUA(U/A)(U/A). Mol. Cell. Biol. 14: 7984–7995.

Levine, T. D., Gao, F., King, P. H., Andrews, L. G., and Keene, J. D. 1993. He1-N1: an autoimmune RNA-binding protein with specificity for 3' uridylate-rich untranslated regions of growth factor mRNAs. Mol. Cell. Biol. 13: 3494–3504.

Levy, N. S., Chung, S., Furneaux, H., and Levy, A. P. 1998. Hypoxic stabilization of vascular endothelial growth factor mRNA by the RNA-binding protein HuR. J. Biol. Chem. 273: 6417–6423.

Ma, W.-J., Cheng, S., Wright, A., Campbell, C., and Furneaux, H. 1996. Cloning and characterization of HuR, a ubiquitously expressed Elav-like protein. J. Biol. Chem. 271: 8144–8151.

Ma, W.-J., Cjung, S., and Furneaux, H. 1997. The elav-like proteins bind to AU-rich elements and to the poly(A) tail of mRNA. Nucl. Acids Res. 25: 3564–3569.

Malter, J. S. 1989. Identification of an AUUUA-specific messenger RNA binding protein. Science 246: 664–666.

Martin, G., and Keller, W. 1998. Tailing and 3'-end labeling of RNA with yeast poly(A) polymerase and various nucleotides. RNA 4: 226–230.

Maquat, L. E. 1995. When cells stop making sense: effects of nonsense codons on RNA metabolism in vertebrate cells. RNA 1: 453–465.

Melton, D. A., Krieg, P. A., Rebagliati, M. R.. Maniatis, T., Zinn, K., and Green, M. R. 1984. Efficient in vitro synthesis of biologically active RNA and RNA hybridization probes from plasmids containing a bacteriophage SP6 promoter. Nudc. Acids Res. 12: 7035–7056.

Muhlrad, D., Decker, C. J., and Parker, R. 1994. Deadenylation of the unstable mRNA encoded by the yeast MFA2 gene leads to decapping followed by 5' to 3' digestion of the transcript. Genes Dev. 8: 855–866.

Myer, V. E., Fan, X. C., and Steitz, J. A. 1997. Identification of HuR as a protein implicated in AUUUA-mediated mRNA decay. EMBO J. 16: 2130–2139.

Nakagawa, J., Waldner, H., Meyer-Monard, S., Hofsteenge, J., Jeno, P., and Moronoi, C. 1995. AUH, a novel gene encoding an AU-specific RNA binding protein with intrinsic enoyl-CoA hydralase activity. Proc. Natl. Acad. Sci. USA 92: 2051–2055.

Peng, S. S.-Y., Chen, C.-Y. A., and Shyu, A.-B. 1996. Functional characterization of a non-AUUUA AU-rich element from the c-jun proto-oncogene mRNA: evidence for a novel class of AU-rich elements. Mol. Cell. Biol. 16: 1490–1499.

Peng, S.-Y., Chen, C.-Y. A., Xu, N., and Shyu, A.-B. 1998. RNA stabilization by the AU-rich element binding protein, HuR, an ELAV protein. EMBO J. 17: 3461–3470.

Presutti, C., Villa, T., Hall, D., Pertica, C., and Bozzoni, 1. 1995. Identification of the cis-elements mediating the autogenous control of ribosomal protein L2 mRNA stability in yeast. EMBO J. 14: 4022–4030.

Qian, Z., and Wilusz, J. 1994. GRSF-1: a poly(A)+ rnRNA binding protein which interacts with a conserved G-rich element. Nucl. Acids Res. 22: 2334–2343.

Ross, J. 1995. mRNA stability in mammalian cells. Microbiol. Rev. 59: 16–95.

Robinow, S., and White, K. 1988. The locus elav of Drosophila melanogaster is expressed in neurons at all developmental stages. Dev. Biol. 126: 294–303.

Schiavi, S. C., Belasco, J. G., and Greenberg, M. E. 1992. Regulation of proto-oncogene mRNA stability. Biochem. Biophys Acta 1114: 95–106.

Shaw, G., and Kamen, R. 1986. A conserved AU rich sequence from the 3' untranslated region of GM-CSF mRNA mediates selective mRNA degradation. Cell 46: 659–667.

Shyu, A.-B., Belasco, J. G., and Greenberg, M. E. 1989. The c-fos transcript is targeted for rapid decay by two distinct mRNA degradation pathways. Genes Dev. 3: 60–72.

Stefanovic, B., Hellerbrand, C., Holcik, M., Briendl, M., Liebhaber, S. A., and Brenner, D. A. 1997. Posttranscriptional regulation of collagen al(I) mRNA in hepatic stellate cells. Mol. Cell. Biol. 17: 5201–5209.

Tarun, S. Z., and Sachs, A. B. 1997. Association of the yeast poly(A) tail binding protein with translation initiation factor eif-4G. EMBO J. 15: 7168–7177.

Vakalopoulou, E., Schaack, J., and Shenk, T. 1991. A 32-kilodalton protein binds to AU-rich domains in the 3' untranslated regions of rapidly degraded mRNAs. Mol. Cell. Biol. 11: 3355–3364.

Weng, Y., Ruiz-Echevarria, M. J., Zhang, S., Cui, Y., Czaplinski, K., Dinman, J. D., and Peltz, S. W. 1997. Characterization of the nonsense-mediated mRNA decay pathway and its effect on modulating translation termination and programmed frameshifting. In "mRNA Metabolism and Post-Transcriptional Gene Regulation", J. B. Harford, D. R. Morris, eds., Wiley-Liss, Inc., New York, pp. 241–263.

Wilson, T., and Treisman, R. 1988. Removal of poly(A) tail and consequent degradation of c-fos mRNA facilitated by 3' AU-rich sequence. Nature 366: 396–399.

Wilusz, J., and Shenk, T. 1988. A 64 kDa nuclear protein binds to RNA segments that include the AAUAAA polyadenylation motif. Cell 52: 221–228.

Wilusz, J., Feig, D. I., and Shenk, T. 1988. The C proteins of heterogeneous nuclear ribonucleoprotein complexes interact with RNA sequences downstream of polyadenylation cleavage sites. Mol. Cell. Biol. 8: 4477–4483.

Wilusz, J., and Shenk, T. 1990. A uridylate tract mediates efficient heterogeneous nuclear ribonucleoprotein C protein-RNA cross-linking and functionally substitutes for the downstream element of the polyadenylation signal. Mol. Cell. Biol. 10: 6397–6407.

Wormington, M., Searfoss, A. M., and Hurney, C. A. 1996. Overexpression of poly(A) binding protein prevents maturation-specific deadenylation and translational inactivation in Xenopus oocytes. EMBO J. 15: 900–909.

Xu, N., Chen, C.-Y. A., and Shyu, A.-B. 1997. Modulation of the fate of cytoplasmic mRNA by AU-rich elements: key sequence features controlling mRNA deadenylation and decay. Mol. Cell. Biol. 17:4611–4621.

Zubiaga, A. M., Belasco, J. G., and Greenberg, M. E. 1995. The nonamer UUAUUUAUU is the key AU-rich sequence motif that mediates inRNA degradation. Mol. Cell. Biol. 15: 2219–2230.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

```
SEQUENCE IDS: 601-1-088
5'-ATTTAGGTGACACTATAGAATACACATTATTTATTATTTATTTATTATTTATTT    (SEQ ID NO:1)
ATTTA-3'

5'-ATTTAGGTGACACTATAGAATACACGTTAGTATTCATTTGTTTACTATTGATTT    (SEQ ID NO:2)
CTTTA-3'

5'-ATTTAGGTGACACTATAGAATACACAAATTTTATTGTGTTTTTAATTTATTTAT    (SEQ ID NO:3)
TAAGATGGATTCTC-3'

5'-ATTATTTATTATTTATTTATTATTTATTATTTA                         (SEQ ID NO:4)

5'-ATTTAGGTGACACTATAGAATACACCCCAACGGGCCCTCCCTCCCCTCCTTGC     (SEQ ID NO:5)
ACCATCATCGCATCACG

5'  AUUAUUUAUUAUUUAUUUAUUAUUUAUUUAUUUA                       (SEQ ID NO:6)

5'-GUCACGUGUCACC                                              (SEQ ID NO:7).

5'-AGCTA$_{60}$ATTGAGGTGCTCGAGGT                              (SEQ ID NO:8)

5'-CATACGATTTAGGTGACACTATAG                                   (SEQ ID NO:9)

5'-ACCTCGAGCACCTC                                             (SEQ ID NO:10)
```

-continued

5'-AGTTAAATAAAT (SEQ ID NO:11)

AUUUA (SEQ ID NO:12)

What is claimed is:

1. An in vitro system that recapitulates regulated RNA deadenylation and degradation of an exogenously added preselected target 3' polyadenylated messenger RNA sequence comprising
   i) a cytoplasmic extract supernatant from a 100,000×g, 1 hour centrifugation isolated from eukaryotic cells or tissues, said extract depleted of activity of proteins that bind polyadenylate;
   ii) a source of ATP; and
   iii) an exogenous target 3' polyadenylated messenger RNA sequence.

2. The system of claim 1 wherein said source of ATP is exogenous.

3. The system of claim 1 wherein said target 3' polyadenylated messenger RNA sequence is selected from the group consisting of an unlabeled 3' polyadenylated messenger target RNA sequence, a labeled 3' polyadenylated messenger target RNA sequence, and a combination thereof.

4. The system of claim 3 wherein said labeled target 3' polyadenylated messenger RNA sequence is labeled with a moiety selected from the group consisting of a fluorescent moiety, a visible moiety, a radioactive moiety, a ligand, and a combination of fluorescent and quenching moieties.

5. The system of claim 1 wherein said cytoplasmic extract is obtained from a cell line selected from the group consisting of HeLa cells and a T cell line.

6. The system of claim 1 wherein said cytoplasmic extract is prepared from cells comprising foreign nucleic acid.

7. The system of claim 1 wherein said cytoplasmic extract is prepared from cells which are infected, stably transfected, or transiently transfected.

8. The systems of claim 1 wherein said cytoplasmic extract is selected from the group consisting of:
   (a) a cytoplasmic extract which contains polyadenylate competitor RNA;
   (b) a cytoplasmic extract which contains a material that sequesters proteins that bind polyadenylate;
   (c) a cytoplasmic extract which contains a proteinase that iactivates proteins that bind to polyadenylate; and
   (d) a cytoplasmic extract which contains an agent that prevents the interaction between polyadenylate and an eddogenous macromolecule that binds to polyadenylate.

9. The system of claim 8 wherein the mnateral that sequesters proteins that bind polyadenylate is selected from the group consisting of:
   (a) antibodies to proteins that bind polyadenylate;
   (b) polyadenylate; and
   (c) a combination of antibodies to proteins that bind polyadenylate, and polyadenylate.

10. The system of claim 9 wherein said material is attached to a matrix.

11. The system of claim 1 wherein said regulated RNA deadenylation and degradation is selected from the group consisting of AU-rich element regulated RNA deadenylation and degradation and C-rich element regulated RNA deadenylation and degradation.

12. The system of claim 1 further comprising a reaction enhancer.

13. The system of claim 12 wherein said reaction enhancer is selected from the group consisting of polyvinyl alcohol, polyvinylpyrrolidone and dextran.

14. The system of claim 13 wherein said reaction enhancer is polyvinyl alcohol.

15. A method for identifying an agent capable of modulating the stability of a target 3' polyadenylated messenger RNA sequence comprising
   (a) providing the system of claim 1;
   (b) introducing said agent into said system;
   (c) determining the extent of deadenylation and degradation of said target 3' polyadenylated messenger RNA sequence; and
   (d) identfying an agent able to modulate the extent of deadenylation and degradation as capable of modulatng the stability of said target 3' polyadenylated messenger RNA sequence.

16. The method of claim 15 wherein said source of ATP is exogenous.

17. The method of claim 15 wherein said target 3' polyadenylated messenger RNA sequence is selected from the group consisting of an unlabeled target 3' polyadenylated messenger RNA sequence, a labeled target 3' polyadenylated messenger RNA sequence, and a combination thereof.

18. The method of claim 17 wherein said labeled target 3' polyadenylated messenger RNA sequence is labeled with a moiety selected from the group consisting of a fluorescent moiety, a visible moiety, a radioactive moiety, a ligand, and a combination of fluorescent and quenching moieties.

19. The method for claim 15 wherein said determining the extent of deadenylation and degradation of said target 3' polyadenylated messenger RNA sequence comprises determining the extent of degradation of said labeled target 3' polyadenylated messenger RNA.

20. The method of claim 15 wherein said agent is an RNA stability modifying molecule.

21. The method of claim 15 wherein said modulating the stability of a target 3' polyadenylated messenger RNA sequence increases the stability of said target RNA sequence.

22. The method of claim 15 wherein said modulating the stability of a target 3' polyadenylated messenger RNA sequence decreases the stability of said RNA sequence.

23. The method of claim 15 wherein said agent is capable of modulating the activity of a AU rich element binding protein or a C-rich element binding protein.

24. The method of claim 23 wherein said AU rich element binding protein is selected from the group consisting of a member of the ELAV protein family; AUF1; tristetraprolin; AUH; TIA; TIAR; glyceraldehyde-3-phosphate; hnRNP C; hnRNP A1; AU-A; and AU-B.

25. The method of claim 24 wherein said member of the ELAV protein family is selected from the group consisting of HuR, Hel-N1, HuC and HuD.

26. A method for identifying an agent capable of modulating the stability of a target 3' polyadenylated messenger RNA sequence in the presence of an exogenously added RNA stability modifier comprising (a) providing the system of claim 1;

(b) introducing said RNA stability modifier into said system;

(c) introducing said agent into said system;

(d) determining the extent of deadenylation and degradation of said 3' polyadenylated messenger RNA sequence; and (e) identifying an agent able to modulate the extent of deadenylation and degradation as capable of modulating the stability of said target 3' polyadenylated messenger RNA sequence in the presence of said exogenously added RNA stability modifier.

27. The method of claim 26, wherein said source of ATP is exogenous.

28. The method of claim 26 wherein said target 3' polyadenylated messenger RNA sequence is selected from the group consisting of an unlabeled target 3' polyadenylated messenger RNA sequence, a labeled target 3' polyadenylated messenger RNA sequence, and a combination thereof.

29. The method of claim 28 wherein said labeled target 3' polyadenylated messenger RNA sequence is labeled with a moiety selected from the group consisting of a fluorescent moiety, a visible moiety, a radioactive moiety, a ligand, and a combination of fluorescent and quenching moieties.

30. The method of claim 28 wherein said determining the extent of deadenylation and degradation of said target 3' polyadenylated messenger RNA sequence comprises determining the extent of degradation of said labeled target 3' polyadenylated messenger RNA.

31. The method of claim 26 wherein said RNA stability modifier increases the stability of said target 3' polyadenylated messenger RNA sequence.

32. The method of claim 31 wherein said agent decreases the stability of said target 3' polyadenylated messenger RNA sequence increased by said RNA stability modifier.

33. The method of claim 26 wherein said RNA stability modifier decreases the stability of said target 3' polyadenylated messenger RNA sequence.

34. The method of claim 33 wherein said agent increases the stability of said target 3' polyadenylated messenger RNA sequence decreased by said RNA stability modifier.

35. The method of claim 26 wherein said agent is capable of modulating the activity of a AU rich element binding protein or a C-rich element binding protein.

36. The method of claim 35 wherein said AU rich element binding protein is selected from the group consisting of a member of the ELAV protein family; AUF1; tristetraprolin; AUH; TIA; TIAR; glyceraldehyde-3-phosphate; hnRNP C; hnRNP A1; AU-A; and AU-B.

37. The method of claim 36 wherein said member of the ELAV protein family is selected from the group consisting of HuR, Hel-N 1, HuC and HuD.

38. A method for identifying an agent capable of modulating the deadenylation and degradation of a target 3' polyadenylated messenger RNA sequence comprising (A) providing the system of claim 1;

(B) introducing said agent into said system;

(C) monitoring the deadenylation and degradation of said target 3' polyadenylated messenger RNA sequence in said system; and (D) identifying an agent able to modulate the extent of said deadenylation and degradation as capable of modulating the deadenylation and degradation of said target polyadenylated messenger RNA sequence.

39. A method for determining whether an endogenous molecule modulates deadenylation or degradation of a target RNA sequence comprising (a) providing the system of claim 1 containing target 3' polyadenylated messenger RNA;

(b) introducing said endogenous molecule into said system; and (c) monitoring the stability of said target 3' polyadenylated messenger RNA sequence in said system thereby determining whether said endogenous molecule is capable of modulating deadenylation and degradation.

40. The method of claim 39 wherein said molecule suspected of participating in the deadenylation or degradation of RNA or regulation thereof is protein or RNA.

41. The method of claim 39 werein the endogenous molecule capable of modulating deadenylation and degradation is an isolated molecule.

42. A method for identifying an agent capable of modulating regulated deadenylation of a target 3' polyadenylated messenger RNA sequence comprising (A) providing a system that recapitulates regulated RNA deadenylation of an exogenously added preselected target 3' polyadenylated messenger RNA sequence comprising
  i) a cytoplasmic extract supernatant from a 100,000×g, 1 hour centrifugation isolated from eukaryotic cells or tissues, said extract depleted of activity of proteins that bind polyadenylate;
  ii) said target 3' polyadenylated messenger RNA sequence;

(B) introducing said agent into said system;

(C) monitoring the deadenylation of said target 3' polyadenylated messenger RNA sequence in said system; and (D) identifying an agent able to modulate the extent of said deadenylation as capable of modulating the regulated deadenylation of said target 3' polyadenylated messenger RNA sequence.

43. A method for determining whether an agent is capable of modulating the degradation of a target 3' polyadenylated messenger RNA sequence in the absence of deadenylation comprising
  (a) providing a cytoplasmic extract supernatant from a 100,000×g, 1 hour centrifigation isolated from eukaryotic cells or tissues, said extract depleted of activity of proteins that bind polyadenylate; a source of ATP; and an exogenous target 3' polyadenylated messenger RNA sequence;
  (b) introducing said agent into said cytoplasmic extract; and
  (c) monitoring the degradation of said target 3' polyadenylated messenger RNA sequence in said extract thereby determining whether said agent is capable of modulating said degradation.

44. A kit for monitoring the stability of a preselected exogenous target 3' polyadenylated messenger RNA sequence under conditions capable of recapitulating regulated RNA deadenylation and degradation, said kit comprising:
  (a) a cytoplasmic extract supematant from a 100,000×g, 1 hour centrifugation, said extract depleted of activity of proteins that bind polyadenylate;
  (b) other reagents; and
  (c) directions for use of said kit.

45. The kit of claim 44 further comprising nucleotide triphosphates, a reaction enhancer, a target RNA sequence, or any combination thereof.

* * * * *

SEQUENCE LISTING

<160> NUMBER OF SEQ ID NOS: 12

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: By
      hybridizing this synthetic oligonucleotide and its appropriate
      complement, template for ARE-A0 RNA were generated.

<400> SEQUENCE: 1
atttaggtga cactatagaa tacacattat ttattattta tttattattt atttattta     59

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence: By
      hybridizing this synthetic oligonucleotide and its appropriate
      complement , templates for MT-ARE-A0 RNA were generated.

<400> SEQUENCE: 2
atttaggtga cactatagaa tacacgttag tattcatttg tttactattg atttcttta     59

<210> SEQ ID NO 3
<211> LENGTH: 68
<212> TYPE: DNA
<213> ORGANISM: Artificial Sequence
<220> FEATURE:
<223> OTHER INFORMATION: Description of Artificial Sequence: By
      hybridizing this synthetic oligonucleotide and its appropriate
      complement , templates for Fos-A0 RNA were generated.

<400> SEQUENCE: 3
atttaggtga cactatagaa tacacaaatt ttattgtgtt tttaatttat ttattaagat     60
ggattctc                                                              68

<210> SEQ ID NO 4
<211> LENGTH: 33
<212> TYPE: DNA
<213> ORGANISM: Artificial Sequence
<220> FEATURE:
<223> OTHER INFORMATION: Description for artificial sequence: Templates
      for SVARE-A0 RNA were generated by inserting the TNF-alpha ARE
      containing this oligonucleotide and its appropriate complement
      between the PstI and Hind

<400> SEQUENCE: 4
attatttatt atttatttat tatttattat tta                                  33

<210> SEQ ID NO 5
<211> LENGTH: 70
<212> TYPE: DNA
<213> ORGANISM: Artificial Sequence
<220> FEATURE:
<223> OTHER INFORMATION: Description of Artificial Sequence: By
      hybridizing this synthetic oligonucleotide and its appropriate complement , templates for CX-A0 RNA were generated.

<400> SEQUENCE: 5
atttaggtga cactatagaa tacaccccaa cgggccctcc ctcccctcct tgcaccatca            60
tcgcatcacg                                                                  70

<210> SEQ ID NO 6
<211> LENGTH: 34
<212> TYPE: RNA
<213> ORGANISM: Artificial Sequence
<220> FEATURE:
<223> OTHER INFORMATION: Description of Artificial Sequence: Synthetic
      RNAs used in competition studies. ARE.

<400> SEQUENCE: 6
auuauuuauu auuuauuuau uauuuauuua uuua                                       34

<210> SEQ ID NO 7
<211> LENGTH: 13
<212> TYPE: RNA
<213> ORGANISM: Artificial Sequence
<220> FEATURE:
<223> OTHER INFORMATION: Description of Artificial Sequence: Synthetic
      RNA used in competition studies contains this sequence.
      Non-specific competitior.

<400> SEQUENCE: 7
gucacguguc acc                                                              13

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: This
      synthetic oligonucleotide and its appropriate complement were
      generated, hybridized, and ligatedto Hind III cut DNA templates.

<400> SEQUENCE: 8
agctatattg aggtgctcga ggt                                                   23

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: SP6
      promoter primer.

<400> SEQUENCE: 9
catacgattt aggtgacact atag                                                  24

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: A specific
      3' end primer for ligated oligonucleotide.

<400> SEQUENCE: 10
acctcgagca cctc                                                             14

<210> SEQ ID NO 11
<211> LENGTH: 12
<212> TYPE: DNA

```
<213> ORGANISM: Artificial Sequence
<220> FEATURE:
<223> OTHER INFORMATION: Description of Artificial Sequence: Antisense
      oligonucleotide.

<400> SEQUENCE: 11
agttaaataa at                                                          12

<210> SEQ ID NO 12
<211> LENGTH: 5
<212> TYPE: RNA
<213> ORGANISM: Artificial Sequence
<220> FEATURE:
<223> OTHER INFORMATION: Description of Artificial Sequence: This
      sequence often repeats in AREs (A-U rich sequence) found in the 3'
      untranslated region of many short-lived mRNAs.

<400> SEQUENCE: 12 auuua                                                                   5
```